(12) United States Patent
Ito et al.

(10) Patent No.: US 11,523,065 B2
(45) Date of Patent: Dec. 6, 2022

(54) IMAGING DEVICE AND GAIN SETTING METHOD

(71) Applicant: SONY CORPORATION, Tokyo (JP)

(72) Inventors: Tomoomi Ito, Tokyo (JP); Nobuhiro Doi, Tokyo (JP); Syohei Uchida, Tokyo (JP); Yusuke Mimura, Tokyo (JP)

(73) Assignee: SONY CORPORATION, Tokyo (JP)

( * ) Notice: Subject to any disclaimer, the term of this patent is extended or adjusted under 35 U.S.C. 154(b) by 14 days.

(21) Appl. No.: 17/059,956

(22) PCT Filed: Apr. 2, 2019

(86) PCT No.: PCT/JP2019/014661
§ 371 (c)(1),
(2) Date: Nov. 30, 2020

(87) PCT Pub. No.: WO2019/235049
PCT Pub. Date: Dec. 12, 2019

(65) Prior Publication Data
US 2021/0218873 A1 Jul. 15, 2021

(30) Foreign Application Priority Data
Jun. 6, 2018 (JP) .............................. JP2018-108890

(51) Int. Cl.
*H04N 5/235* (2006.01)
*G03B 7/095* (2021.01)

(52) U.S. Cl.
CPC .......... *H04N 5/2352* (2013.01); *G03B 7/095* (2013.01)

(58) Field of Classification Search
CPC ......... H04N 5/2352; H04N 2005/2255; H04N 5/2353; H04N 5/3532; H04N 5/2351;
(Continued)

(56) References Cited

U.S. PATENT DOCUMENTS 5,428,421 A * 6/1995 Kawahara .............. H04N 5/238
348/E5.04
6,356,304 B1 * 3/2002 Kawaguchi ............ H04N 5/238
348/E5.064
(Continued)

FOREIGN PATENT DOCUMENTS

CN 106254787 A 12/2016
JP 2010-074313 A 4/2010
(Continued)

OTHER PUBLICATIONS

Machine Translation of JP-2014022943-A (Year: 2014).*
(Continued)

*Primary Examiner* — Jason A Flohre
(74) *Attorney, Agent, or Firm* — Chip Law Group

(57) ABSTRACT

To suppress a difference in brightness and darkness in a captured image caused by a difference in an exposure start time by a rolling shutter even if the exposure period is not changed. Provided is an imaging device including a gain setting unit configured to set a gain for each line in which a plurality of pixels is arrayed, the plurality of pixels being two-dimensionally arranged in a matrix in an image sensor, on the basis of diaphragm drive information regarding a diaphragm drive locus representing a time-series change in a diaphragm value. Thereby, the difference in brightness and darkness in a captured image caused by the difference in an exposure start time by a rolling shutter can be suppressed even if the exposure period is not changed.

14 Claims, 14 Drawing Sheets

(58) Field of Classification Search
CPC ........ H04N 5/238; H04N 5/243; G03B 7/095;
G03B 7/093; G03B 15/14; A61B 34/30;
A61B 90/361; A61B 2034/301
See application file for complete search history.

(56) References Cited

U.S. PATENT DOCUMENTS

| | | | | |
|---|---|---|---|---|
| 2008/0267608 | A1* | 10/2008 | Kubota | H04N 5/2353 |
| | | | | 348/E5.022 |
| 2010/0066897 | A1* | 3/2010 | Miyanari | H04N 5/3532 |
| | | | | 348/E5.034 |
| 2016/0366324 | A1* | 12/2016 | Nakata | G03B 7/097 |
| 2018/0234605 | A1* | 8/2018 | Hisamoto | H04N 5/2351 |

FOREIGN PATENT DOCUMENTS

| | | | |
|---|---|---|---|
| JP | 2013-031010 | A | 2/2013 |
| JP | 2014-022943 | A | 2/2014 |
| JP | 2014022943 | A * | 2/2014 |
| JP | 2015-104003 | A | 6/2015 |
| JP | 2017-003830 | A | 1/2017 |

OTHER PUBLICATIONS

International Search Report and Written Opinion of PCT Application No. PCT/JP2019/014661, dated Jun. 25, 2019, 12 pages of ISRWO.

* cited by examiner

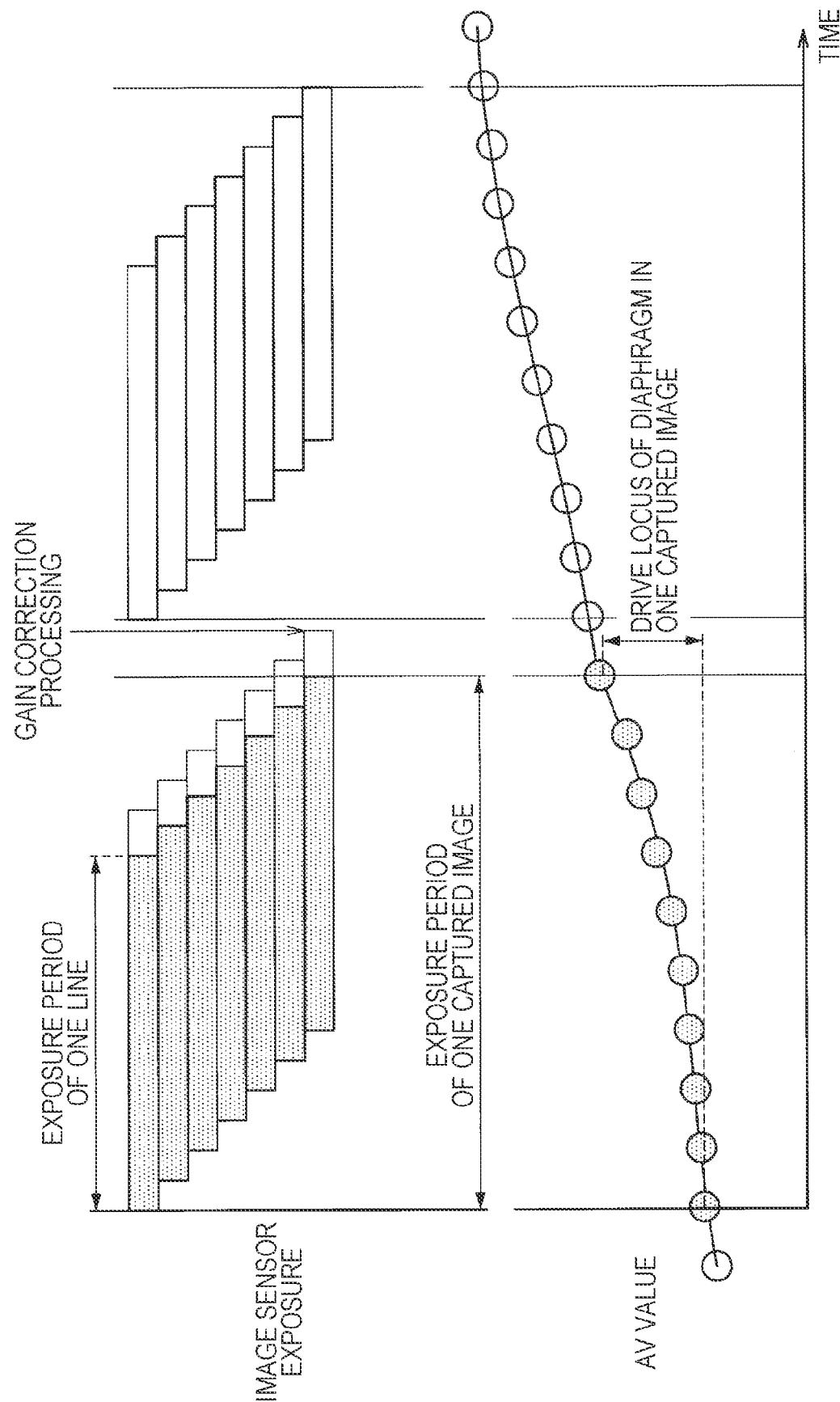

IMAGING DEVICE AND GAIN SETTING METHOD

CROSS REFERENCE TO RELATED APPLICATIONS

This application is a U.S. National Phase of International Patent Application No. PCT/JP2019/014661 filed on Apr. 2, 2019, which claims priority benefit of Japanese Patent Application No. JP 2018-108890 filed in the Japan Patent Office on Jun. 6, 2018. Each of the above-referenced applications is hereby incorporated herein by reference in its entirety.

TECHNICAL FIELD

The present disclosure relates to an imaging device, a gain setting method, and a program.

BACKGROUND ART

In recent years, in an imaging device such as a digital camera or a digital video camera, various technologies have been developed to improve performance of the entire imaging device. Recently, in particular, an imaging device equipped with a complementary metal oxide semiconductor (CMOS) image sensor, as described in Patent Document 1, has become common, and technical improvement regarding the CMOS image sensors is expected.

The CMOS image sensor reads each of arrayed pixels by a rolling shutter method, and the imaging device applies processing to a signal acquired from the image sensor and displays a captured image. In the readout by the rolling shutter method, an exposure start time and an exposure end time are different among horizontal lines from a first read horizontal line to a last read horizontal line. When a diaphragm of an imaging device changes during exposure of horizontal lines having different exposure start times, light amounts accumulated in the upper and lower horizontal lines differ, and a difference in brightness and darkness occurs between upper and lower portions in one captured image.

When the captured image having the difference in brightness and darkness is displayed, a screen flickers, and the entire screen is displayed in black or white. In particular, when the captured image is continuously displayed in live view or the like, effects of screen flickering, blackout, white highlights, or the like are significant. When the difference in brightness and darkness occurs in the captured image in this way, the quality of the captured image deteriorates. Furthermore, when a user tracks an object as a moving body, the object becomes difficult to track and the user loses a capture opportunity, which deteriorates performance of the entire imaging device.

As a technology of suppressing the difference in brightness and darkness between upper and lower portions of a captured image, Patent Document 1 discloses a technology of suppressing the difference in brightness and darkness between upper and lower portions of a captured image by correcting an exposure period.

CITATION LIST

Patent Document

Patent Document 1: Japanese Patent Application Laid-Open No. 2017-3830

SUMMARY OF THE INVENTION

Problems to be Solved by the Invention

However, for example, a shutter speed may be restricted or suppression of the difference in brightness and darkness may be insufficient by correcting the exposure period, and further development of the technology of suppressing the difference in brightness and darkness between upper and lower portions of a captured image is expected.

Therefore, in view of the foregoing, it is desirable to suppress the difference in brightness and darkness in a captured image caused by a difference in an exposure start time by a rolling shutter even if the exposure period is not changed.

Solutions to Problems

According to the present disclosure, provided is an imaging device including a gain setting unit configured to set a gain for each line in which a plurality of pixels is arrayed, the plurality of pixels being two-dimensionally arranged in a matrix in an image sensor, on the basis of diaphragm drive information regarding a diaphragm drive locus representing a time-series change in a diaphragm value.

Furthermore, according to the present disclosure, provided is a gain setting method including, by a processor, setting a gain for each line in which a plurality of pixels is arrayed, the plurality of pixels being two-dimensionally arranged in a matrix in an image sensor, on the basis of diaphragm drive information regarding a diaphragm drive locus representing a time-series change in a diaphragm value.

Furthermore, according to the present disclosure, provided is a program for causing a computer to function as a gain setting unit configured to set a gain for each line in which a plurality of pixels is arrayed, the plurality of pixels being two-dimensionally arranged in a matrix in an image sensor, on the basis of diaphragm drive information regarding a diaphragm drive locus representing a time-series change in a diaphragm value.

According to the present disclosure, a gain is set for each line, so that correction to suppress a difference between light amounts acquired by lines can be performed.

Effects of the Invention

As described above, according to the present disclosure, the difference in brightness and darkness in a captured image caused by the difference in the exposure start time by the rolling shutter can be suppressed even if the exposure period is not changed.

Note that the above-described effect is not necessarily limited, and any of effects described in the present specification or another effect that can be grasped from the present specification may be exerted in addition to or in place of the above-described effect.

BRIEF DESCRIPTION OF DRAWINGS

FIG. 2 is a diagram illustrating exposure of lines of a CMOS image sensor and a locus of a diaphragm of the imaging device.

MODE FOR CARRYING OUT THE INVENTION

A favorable embodiment of the present disclosure will be described in detail with reference to the appended drawings. Note that, in the present specification and drawings, redundant description of configuration elements having substantially the same functional configuration is omitted by providing the same sign.

Note that the description will be given in the following order.

1. Appearance of Example to Which Technology of Present Disclosure is Applied
2. Background
3. Function and Configuration of Imaging Device
4. Gain Correction
5. Operation Flow
6. Modification
7. Hardware Configuration Example
8. Application (1. Appearance of Example to Which Technology of Present Disclosure is Applied)

Figure 1A:
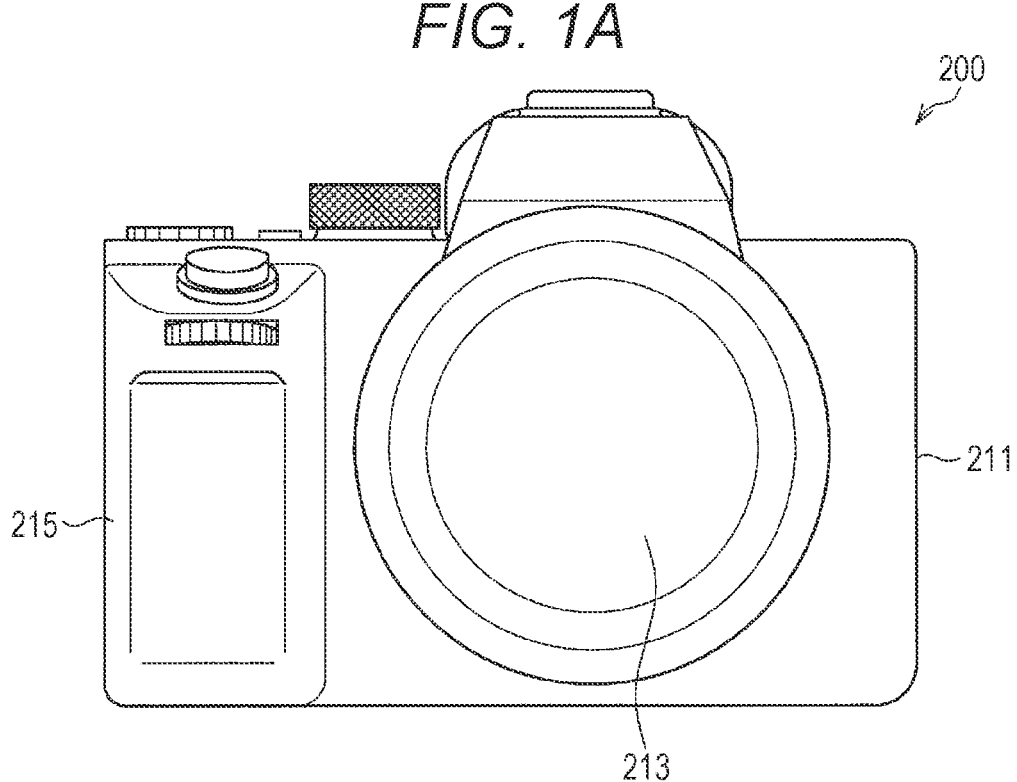
FIG. 1A is an external view of an imaging device according to an embodiment of the present disclosure.
Figure 1B:
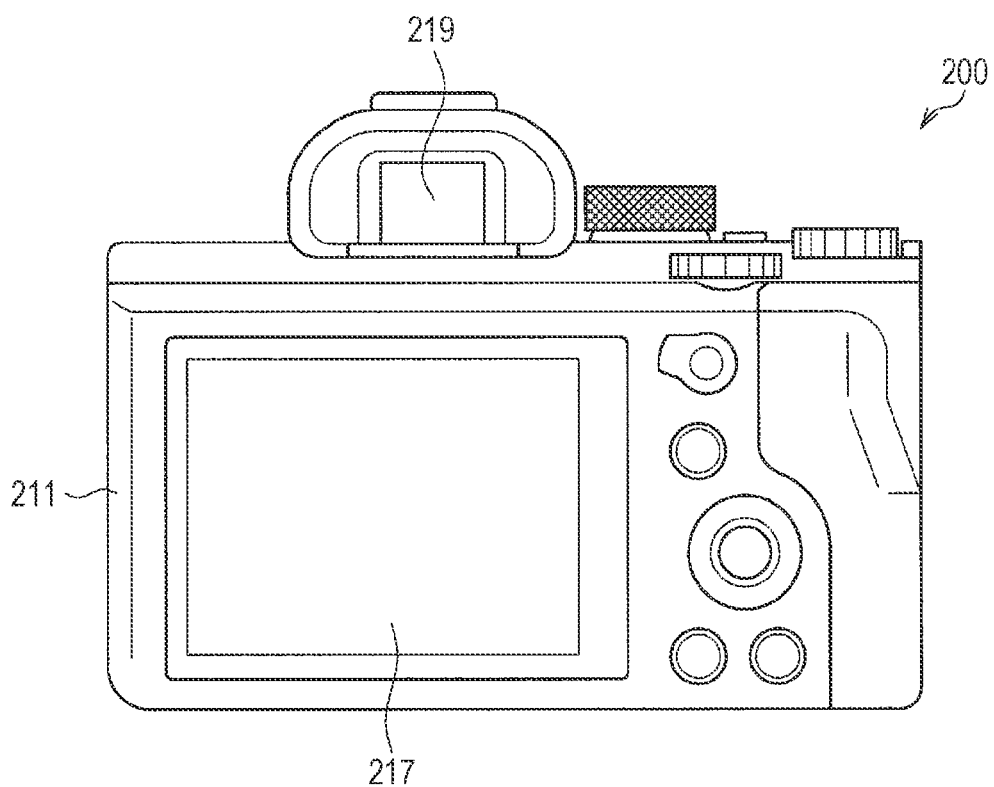
FIG. 1B is an external view of the imaging device according to the embodiment of the present disclosure.

An example of an electronic device to which the technology of the present disclosure is applied will be described with reference to FIGS. 1A and 1B. FIGS. 1A and 1B are views illustrating a digital camera to which the technology of the present disclosure is applied. A digital camera 200 includes a main body (camera body) 211, an interchangeable lens unit 213, a grip part 215 held by a user at the time of capturing an image, a monitor part 217 for displaying various types of information, and an electronic view finder (EVF) 219 for displaying a through image observed by the user at the time of capturing an image. Note that FIG. 1A is an external view of the digital camera 200 viewed from the front (that is, an object side), and FIG. 1B is an external view of the digital camera 200 viewed from the rear (that is, a photographer side).

The technology of the present disclosure is used when, for example, the digital camera 200 captures an image, and in particular, can prevent flickering, blackout, white highlights, or the like of a captured image in live view display on the monitor part 217. Note that in the live view display, the captured image formed by processing a signal obtained from an image sensor is displayed in real time. In the live view display, the user can determine composition of an object and can track the object when the object is a moving body.

(2. Background)

Recently, a CMOS image sensor is generally mounted on the digital camera 200. First, the CMOS image sensor will be described.

FIG. 2 is a diagram illustrating exposure of lines of the CMOS image sensor and a locus of a diaphragm of the imaging device. FIG. 2 illustrates an exposure period of each horizontal line of the image sensor in the upper part and a conceptual diagram of elapsed time and a change in diaphragm value in the lower part. In the CMOS image sensor, a plurality of pixels is arranged in a horizontal direction and a vertical direction, and signals are read from the pixels by a rolling shutter method for sequentially reading each horizontal line. A horizontal axis length of one horizontal line indicates the exposure period in the horizontal line, and charges are accumulated in the pixels arranged in the each line during this exposure period. After that, the accumulated charges are sequentially read for each line. The exposure of one captured image is completed from the start of exposure of an uppermost line to the end of exposure of a lowermost line. In FIG. 2, the diaphragm changes during this exposure.

Here, the diaphragm will be described. The diaphragm is a configuration for adjusting the amount of light incident through a lens, and is provided in the lens unit 213 of the digital camera 200. The diaphragm adjusts the amount of light taken in by changing a shielding area for the lens. The light taken in by the digital camera 200 is adjusted according to a difference in the shielding area with respect to the lens caused by the diaphragm, and a numerical value representing a light amount is taken as a diaphragm value (AV value).

As the AV value increases, the diaphragm is narrowed and the shielding area for the lens is widened. Therefore, the light amount passing through the lens decreases. On the other hand, as the AV value decreases, the diaphragm is opened and the shielding area for the lens is narrowed. Therefore, the light amount passing through the lens increases. Such an AV value is changed for optimizing the quality of the captured image when the object is captured.

FIG. 2 illustrates an example of raising the AV value in the digital camera 200 equipped with the CMOS image sensor. The AV value rises from when the exposure of one captured image is started to when the exposure is completed. At this time, the light amount acquired in each horizontal line is different. Therefore, the captured image that includes the difference in the light amount in each horizontal line may have a difference in brightness and darkness between upper and lower parts. When the difference in brightness and darkness occurs in one captured image as described above, flickering, blackout, white highlights, or the like of the captured image occurs, and the object becomes difficult to track by the user, and the quality of the captured image deteriorates.

Therefore, the inventors of the present disclosure have diligently studied a technology of suppressing the difference in brightness and darkness in a captured image, which occurs due to a difference in exposure start time in the rolling shutter method, and have conceived the technology of the present disclosure. For example, a technical outline will be described using the lowermost horizontal line illustrated in FIG. 2. The exposure is sequentially started from the uppermost horizontal line, and after the exposure is performed for a certain period of time, the charges are read from the pixels in each horizontal line. In the technology of the present disclosure, for example, a gain calculated on the basis of a diaphragm drive locus representing a time-series change in the diaphragm value is set for the lowermost horizontal line, and gain correction processing is applied, so that the difference in brightness and darkness in upper and lower parts of one captured image is suppressed.

That is, in the technology of the present disclosure, a gain is set for a plurality of horizontal lines of an image sensor having a plurality of pixels arrayed in the horizontal direction and the vertical direction on the basis of diaphragm drive information regarding the diaphragm drive locus representing the time-series change in the diaphragm value. Thereby, gain correction with a suppressed change in the light amount due to driving of the diaphragm becomes possible for the light amount acquired from each horizontal line. Therefore, the difference in brightness and darkness in the captured image can be suppressed.

The imaging device to which the technology of the present disclosure is not limited. Hereinafter, the technology of the present disclosure will be described by taking an interchangeable lens-type imaging device as an example.

(3. Function and Configuration of Imaging Device)

Figure 3:
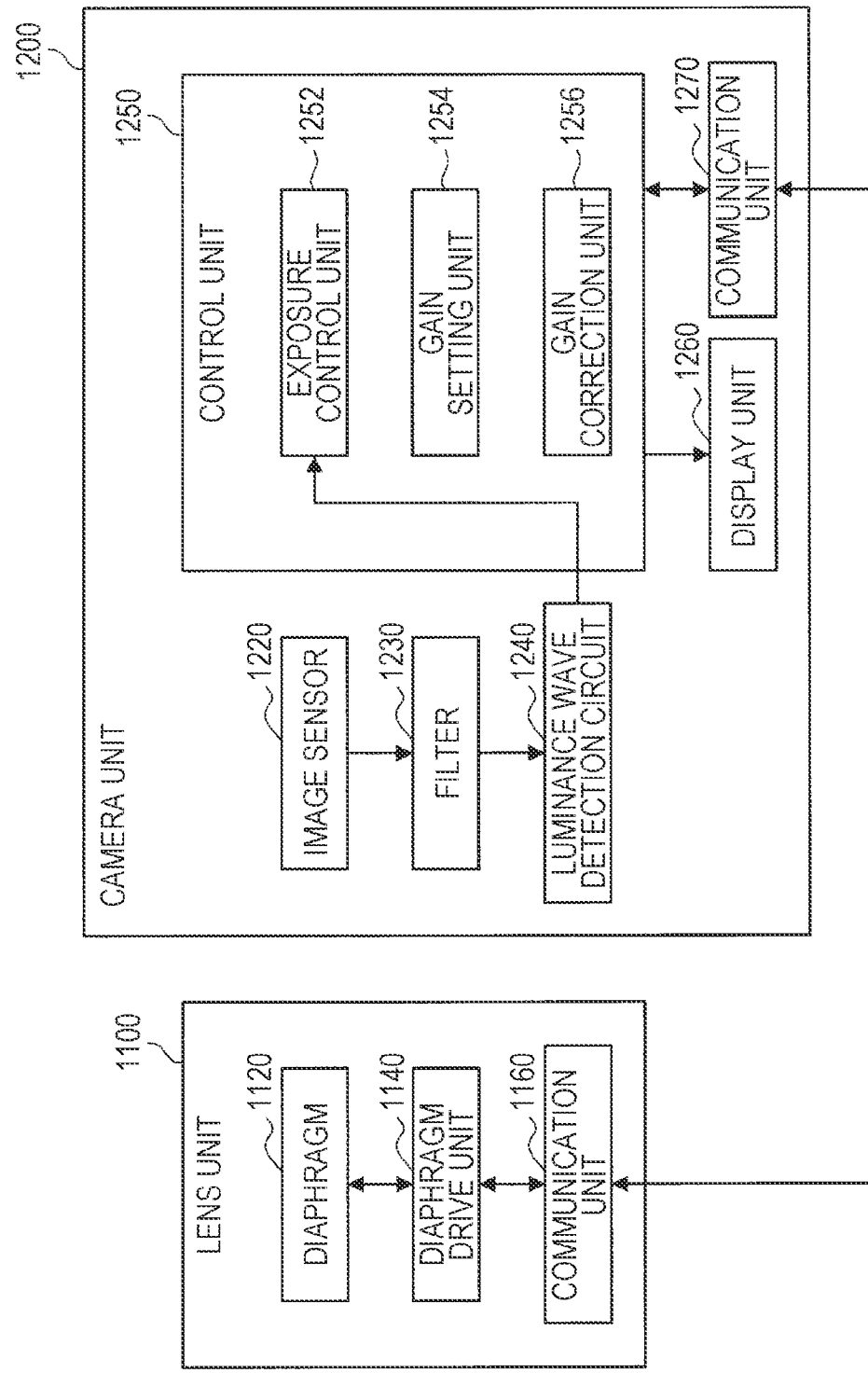
FIG. 3 is a block diagram for describing the imaging device according to the embodiment.

Function and configuration of the imaging device according to the embodiment of the present disclosure will be described with reference to FIG. 3. Referring to FIG. 3, an imaging device 1000 according to the present embodiment includes a lens unit 1100 and a camera unit 1200.

The lens unit 1100 includes a diaphragm 1120, a diaphragm drive unit 1140, and a communication unit 1160. The lens unit 1100 has a function to adjust a light amount acquired by an image sensor 1220 provided in the camera unit 1200 when the diaphragm is driven.

The diaphragm 1120 has a function to adjust the amount of light entering through a lens. An aperture diameter of the diaphragm 1120 is controlled in response to an instruction or the like from the diaphragm drive unit 1140. The diaphragm 1120 also has a function to acquire the AV value of the diaphragm by a diaphragm detection sensor (not illustrated).

The diaphragm drive unit 1140 drives the diaphragm 1120 included in the lens unit 1100. The diaphragm drive unit 1140 includes an actuator, a driver, and the like for driving the diaphragm, in addition to the diaphragm. The AV value is changed in the diaphragm drive unit 1140 via the actuator and driver. Furthermore, the diaphragm drive unit 1140 acquires information output from an exposure control unit 1252 via the communication unit 1160 and a communication unit 1270 and can drive the diaphragm.

The diaphragm drive unit 1140 also has a function to output diaphragm drive information regarding diaphragm driving of the diaphragm 1120 to the camera unit 1200. The diaphragm drive information regarding diaphragm driving includes information such as a current diaphragm value, luminance information of an object, and a distance to the object.

The communication unit 1160 has a function to output the diaphragm drive information regarding diaphragm driving acquired from the diaphragm drive unit 1140 to the camera unit 1200 and to acquire a diaphragm drive information regarding the diaphragm drive locus from the camera unit 1200. The lens unit 1100 and the camera unit 1200 may continuously or temporarily perform communication or may perform communication at a predetermined interval via the communication unit 1160.

Next, the camera unit 1200 will be described. The camera unit 1200 includes an image sensor 1220, a filter 1230, a luminance wave detection circuit 1240, a control unit 1250, a display unit 1260, and a communication unit 1270. The camera unit 1200 has a function to acquire the diaphragm drive information regarding diaphragm driving acquired from the lens unit 1100 and output control information for adjusting the diaphragm provided in the lens unit 1100. Furthermore, the camera unit 1200 has a function to perform the gain correction processing for a signal read from the image sensor 1220, and display a captured image with a suppressed difference in brightness and darkness on the display unit 1260.

The image sensor 1220 is, for example, a CMOS image sensor having a plurality of pixels two-dimensionally arranged in a matrix. The image sensor 1220 has a function to read a light beam of the object received through the lens unit 1100 as a signal and output the signal.

The filter 1230 has a function to generate a color component regarding the light beam of the object received by the image sensor 1220 and the like, and output a signal to which the color component is added.

The luminance wave detection circuit 1240 has a function to output luminance information of the light beam of the object received by the image sensor 1220 to the exposure control unit 1252.

The control unit 1250 includes an exposure control unit 1252, a gain setting unit 1254, and a gain correction unit 1256. The control unit 1250 has a function to generate the control information for adjusting the diaphragm 1120 provided in the lens unit 1100, using the signal obtained from the image sensor 1220, and output the control information to the lens unit 1100. Furthermore, the control unit 1250 has a function to perform the gain correction for the signal obtained from the image sensor 1220, and suppress the difference in brightness and darkness of the captured image displayed on the display unit 1260.

The exposure control unit 1252 calculates a drive locus of the diaphragm representing a time-series change in the AV value from the current AV value to when reaching a target AV value according to the signal obtained from the image sensor 1220 and the diaphragm drive information regarding the diaphragm drive locus obtained from the lens unit 1100 and the like. When calculating the drive locus of the diaphragm, the exposure control unit 1252 determines a diaphragm drive start scheduled time when driving of the diaphragm is started. When the drive locus of the diaphragm is predicted in advance, the prediction is performed before exposure of a setting target frame for which the gain to be described below is to be set is started.

The exposure control unit 1252 performs calculation on the basis of various types of information when calculating the drive locus of the diaphragm. Hereinafter, the information used when calculating the drive locus of the diaphragm, the calculated drive locus of the diaphragm, and actual values of diaphragm driving will be referred to as diaphragm drive information regarding the drive locus of the diaphragm, and description will be given.

The diaphragm drive information regarding the drive locus of the diaphragm includes information regarding driving of the diaphragm, and specifically, information of time to start and end the drive locus of the diaphragm. Furthermore, the diaphragm drive information regarding the drive locus of the diaphragm includes a lens state at the time when the drive locus of the diagram that is the information regarding driving of the diaphragm is started, diaphragm drive parameter information, and the like.

The lens state is information indicating a relationship between the object and the lens, such as a focus position and a zoom position. The diaphragm drive parameter is a drive speed of the diaphragm, a drive mode of the diaphragm, and the like.

Examples of the drive mode of the diaphragm include silent drive, high-speed drive, and the like. A suitable drive mode is set according to an image capture scene or a user setting. The imaging device 1000 calculates the drive locus of the diaphragm on the basis of the diaphragm drive information regarding driving of the diaphragm.

Here, the target AV value used when calculating the drive locus of the diaphragm will be described. The target AV value may be automatically set by the imaging device 1000 or may be set by the user. Hereinafter, the case where the target AV value is automatically set will be described.

The imaging device 1000 automatically performs exposure control for optimizing the quality of the captured image according to the image capture scene or the like. In the exposure control, an EV value that gives proper exposure is determined. The EV value indicates the degree of brightness. An expression (APEX relational expression) used for the automatic exposure control is given in the following expression (1).

[Math. 1]

$$BV+SV=TV+AV \quad (1)$$

Note that BV, SV, TV, and AV are a numerical sequence represented by logarithmic values with base 2 for values of object luminance, ISO sensitivity, shutter speed T, and diaphragm F, respectively. The above expression (1) can be further expressed as the following expression (2).

[Math. 2]

$$EV=TV+AV \quad (2)$$

Furthermore, AV and TV can be defined by the following expressions (3) and (4).

[Math. 3]

$$AV=2\log_2 F \quad (3)$$

[Math. 4]

$$TV=-\log_2 T \quad (4)$$

When the diaphragm F is 1, the AV value is 0, and when the diaphragm F is other than 1, the AV value can be counted as in the following table (1).

TABLE 1

| F | 1 | 1.4 | 2 | 2.8 | 4 | 5.6 | 8 | 11 | 16 | 22 |
|---|---|-----|---|-----|---|-----|---|----|----|----|
| AV | 0 | 1 | 2 | 3 | 4 | 5 | 6 | 7 | 8 | 9 |

An F value is a value obtained by dividing a focal length by an effective aperture of the lens. The F value being doubled means that the effective aperture is halved, and the lens area that takes in light becomes ¼. When the F value becomes √2 times, the lens area that takes in light is halved, so the exposure is halved. For example, in a case of obtaining the same EV value, when the diaphragm F is driven and the brightness is doubled to obtain the AV value that becomes a one-level smaller value, the numerical sequence TV for the shutter speed needs to be set to a one-level larger value to half the exposure time.

The TV value can be counted according to the shutter speed (second) T as in the following table (2).

TABLE 2

| T | 4 | 2 | 1 | ½ | ¼ | ⅛ | 1/15 |
|---|---|---|---|---|---|---|------|
| TV | −2 | −1 | 0 | 1 | 2 | 3 | 4 |
| T | 1/30 | 1/60 | 1/125 | 1/250 | 1/500 | 1/1000 | |
| TV | 5 | 6 | 7 | 8 | 9 | 10 | |

For example, in the case of capturing an image with the diaphragm F4 at the shutter speed of 1/250, the AV value becomes 4 and the TV value becomes 8. Therefore, when capturing an image with the diaphragm F4 at the shutter speed of 1/250, EV=12 is obtained. Furthermore, when capturing an image with the diaphragm F5.6 at the shutter speed of 1/125, EV=12 is obtained. From the above, it is understood that the appropriate exposure EV can be determined by changing the diaphragm F or the shutter speed T.

The ISO sensitivity indicates a film speed, and a high-speed shutter is released in proportion to the ISO sensitivity. The proper exposure EV can change depending on settings of the ISO sensitivity. For example, when the ISO sensitivity is increased to 100 to 200 to enhance the image capture sensitivity, the EV value at the ISO sensitivity of 200 increases by +1 from the EV value at the ISO sensitivity of 100.

The exposure control unit 1252 calculates an appropriate AV value for proper exposure, that is, for acquiring an optimized captured image, by automatic exposure control function using the above-described relationship. In the automatic exposure control function, for example, the object luminance is measured using a sensor built-in the imaging device 1000 and the BV value is calculated, and the AV value can be determined according to the SV value and the TV value of the imaging device. As described above, the exposure control unit 1252 automatically determines the target AV value so that the captured image can be captured with proper exposure. At this time, the TV value may be a fixed value.

Note that an example in which the exposure control unit 1252 calculates the target AV value by the automatic exposure control function has been described. However, the target AV value may be determined by the user. When the target AV value is determined in this way, the exposure control unit 1252 calculates the diaphragm drive locus using the lens state, the diaphragm drive parameter information, and the like.

An example in which the exposure control unit 1252 is provided in the camera unit 1200 has been described. However, where to provide the exposure control unit 1252 is not limited as long as the diaphragm drive information regarding the diaphragm drive locus can be acquired. For example, the exposure control unit 1252 may be included in the lens unit 1100. In the case where the exposure control unit 1252 is included in the camera unit 1200, the diaphragm drive information regarding the drive locus of the diaphragm including the object luminance, the object distance, and the like is acquired from the lens unit 1100 and calculation is performed. Furthermore, in the case where the exposure control unit 1252 is provided in the lens unit 1100, the diaphragm drive information regarding the drive locus of the diaphragm including the target AV value, the drive mode, and the like is acquired from the camera unit 1200, and the drive locus of the diaphragm is calculated.

When calculating the drive locus of the diaphragm, the exposure control unit 1252 outputs the drive locus of the diaphragm to the diaphragm drive control unit 1120.

Next, the gain setting unit 1254 will be described. The gain setting unit 1254 has a function to calculate and set a gain correction amount on the basis of the diaphragm drive information regarding the diaphragm drive locus calculated by the exposure control unit 1252. The imaging device 1000 can suppress the difference in brightness and darkness in the captured image by performing the gain correction on the basis of the calculated gain correction amount. The method of calculating the gain correction amount will be described below.

Furthermore, in a case of requiring adjustment of the exposure period when calculating the gain correction amount, the gain setting unit 1254 may adjust the exposure period and calculate the gain correction amount on the basis of the adjusted exposure period.

The gain correction unit 1256 has a function to perform the gain correction on the basis of the gain correction amount set by the gain setting unit 1254, and output the captured image for which the gain correction has been performed to the display unit 1260.

The display unit 1260 has a function to display the captured image for which the gain correction has been performed for the user. The display unit 1260 may be, for example, a liquid crystal display, an organic electro luminescence (EL) display, or the like.

A touch sensor (not illustrated) that detects a touch of a user's finger may be provided on a screen of the display unit 1260. The touch sensor may be used when the user inputs an operation to the imaging device. Examples of a touch sensor method include a capacitance method, a resistance film method, and the like, but the touch sensor method is not particularly limited.

A live view image may be displayed on the display unit 1260. The live view image is an image displayed on the display unit 1260 for the user to confirm an angle of view, for example. The live view image is displayed on the screen by displaying image data in real time, the image data being obtained by performing image processing for a charge signal acquired from the image sensor 1220.

A reproduced image may be displayed on the display unit 1260. The reproduced image is an image displayed on the display unit 1260 for the user to confirm a captured still image or moving image. The reproduced image is displayed on the display unit 1260 by reading and displaying an image stored in a storage unit (not illustrated). The gain correction according to the technology of the present disclosure may be performed for the live view image displayed on the display unit 1260 or may be separately performed when the image stored in the storage unit is read.

The communication unit 1270 has a function to acquire information to be used by the control unit 1250 from the lens unit 1100 and output information to be used by the lens unit 1100 from the camera unit 1200, between the camera unit 1200 and the lens unit 1100. The communication unit 1270 may continuously or temporarily perform communication or may perform communication at a predetermined interval between the camera unit 1200 and the lens unit 1100.

(4. Gain Correction)

Figure 4:
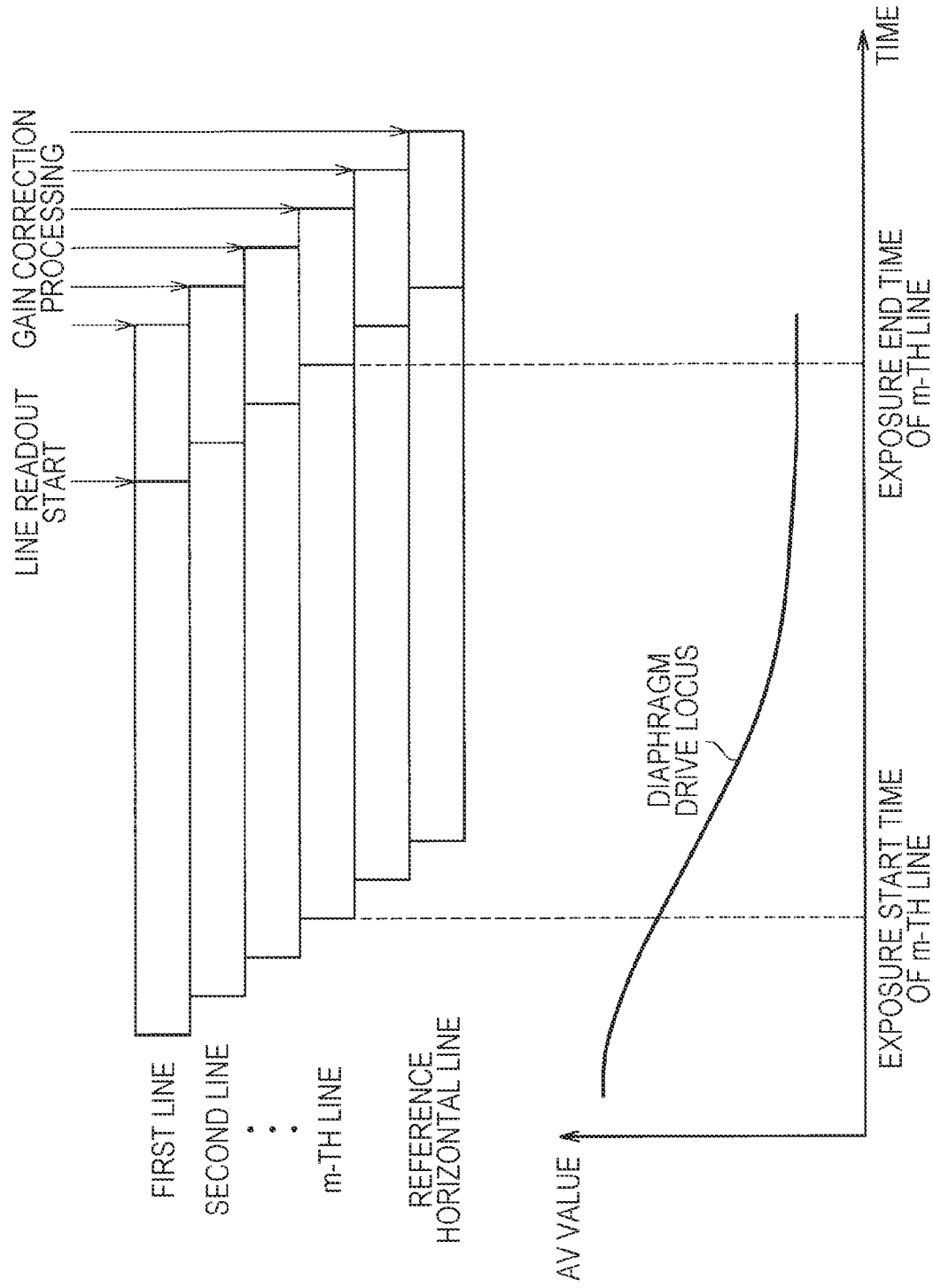
FIG. 4 is a diagram illustrating exposure of lines of a CMOS image sensor and a locus of a diaphragm of the imaging device of when gain correction is performed.

The gain correction will be described with reference to FIG. 4. FIG. 4 is a conceptual diagram of the diaphragm and exposure of lines of the image sensor of when the gain correction is performed. In each horizontal line, charges are accumulated in each pixel for a certain period of time after the exposure is started, and the exposure is completed. After the exposure is completed, signal readout of the horizontal line is performed for a predetermined time. Thereafter, the gain correction processing is performed on the basis of the gain set by the gain setting unit.

In FIG. 4, the diaphragm value of the diaphragm drive locus decreases with time. Therefore, the light amount acquired by each horizontal line gradually rises from when the exposure of the uppermost line (first line) is started to when the exposure of the lowermost line is completed. In the gain correction, the gain setting unit 1254 calculates the gain correction amount of each horizontal line such that displacement of a difference in the light amount in each horizontal line becomes small, and the gain correction unit 1256 performs the gain correction on the basis of the gain correction amount.

Specifically, for example, when the AV value change in FIG. 4 is taken as an example, the light amount acquired by the first line is smaller than the light amount acquired by the second line because the AV value tends to decrease. In this case, the gain setting unit 1254 is only required to set the gain of a larger value for the first line than for the second line.

Figure 5:
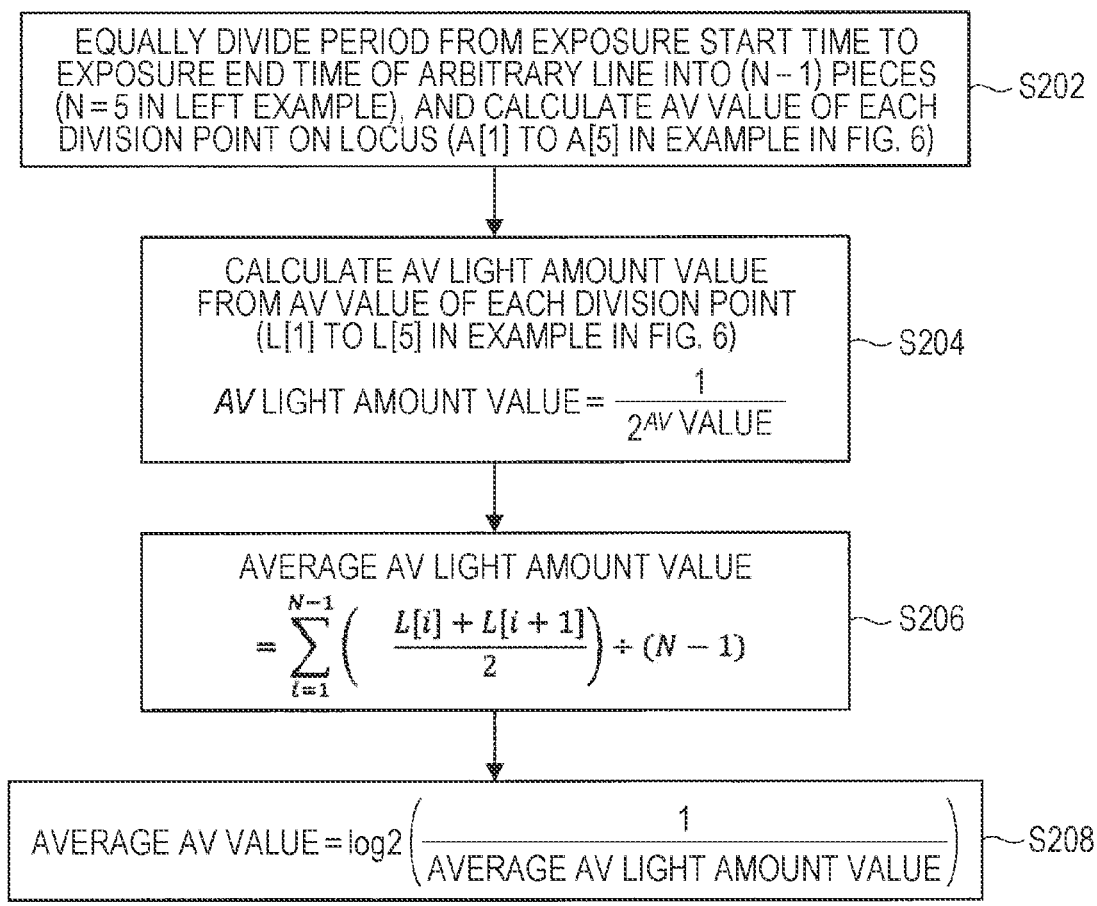
FIG. 5 is a diagram illustrating a flow of calculating an average AV value.
Figure 6:
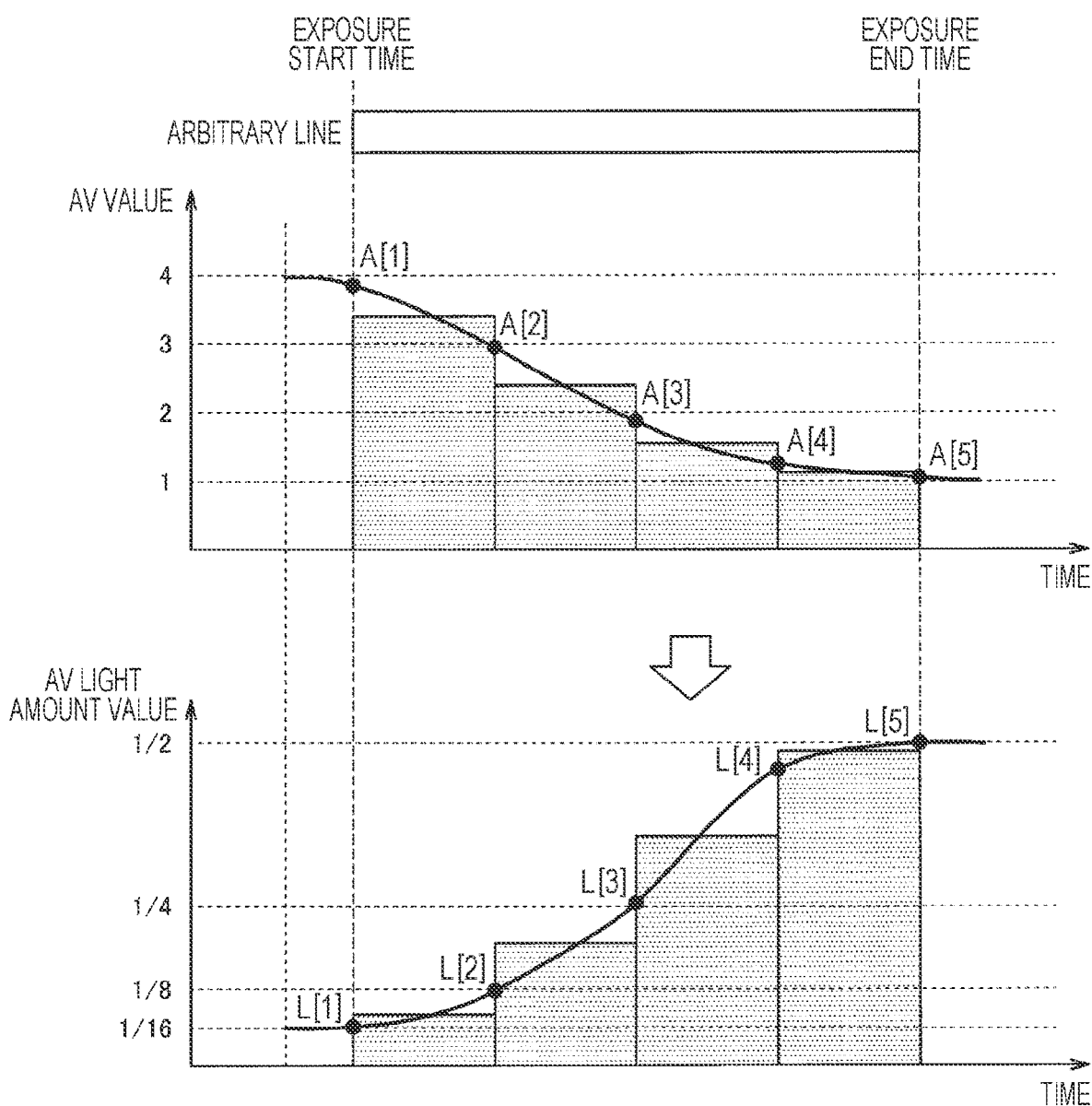
FIG. 6 is a diagram illustrating a relationship between a change in a diaphragm value and a change in a light amount in an arbitrary horizontal line.

That is, the gain setting unit 1254 is only required to set a higher value for the second horizontal line than for the first horizontal line as the gain, the second horizontal line having a higher average AV value in the exposure period than the first horizontal line, on the basis of the diaphragm drive locus. Here, the average AV value indicates an average value of the AV values from the exposure start to the exposure end of each horizontal line. The average AV value will be described below with reference to FIGS. 5 and 6. FIG. 5 is a diagram illustrating a flow of calculating the average AV value, and FIG. 6 is graphs illustrating a relationship between a change in the diaphragm value and a change in the light amount in an arbitrary horizontal line.

First, the gain setting unit 1254 equally divides the period from the exposure start time to the exposure end time of an arbitrary line into (N−1) pieces, and calculates the AV value at each division point on the diaphragm drive locus (S202). FIG. 6 illustrates the diaphragm drive locus in the exposure period of an arbitrary line, and illustrates a state where the exposure period of an arbitrary line is equally divided into four periods. Moreover, the AV value at an equal division point is illustrated as A[N].

Next, the gain setting unit 1254 calculates an AV light amount value L[i] from the AV value A[N] of each division point using the following expression (5) (S204). From the following expression (5), when the AV value increases by 1, the AV light amount value passing through the aperture diameter of the diaphragm is halved. In the lower graph in FIG. 6, the AV value A[N] is converted into the AV light amount value L[i].

[Math. 5]

$$AV \text{ LIGHT AMOUNT VALUE} = \frac{1}{2^{AV\ VALUE}} \quad (5)$$

Moreover, the gain setting unit 1254 calculates an average of the AV light amount values L[i] at the respective division points calculated using the expression (5), using the following expression (6).

[Math. 6]

$$\text{AVERAGE } AV \text{ LIGHT AMOUNT VALUE} = \sum_{i=1}^{N-1}\left(\frac{L[i]+L[i+1]}{2}\right) \div (N-1) \quad (6)$$

Finally, the gain setting unit 1254 converts the average AV light amount value obtained using the above expression (6) into the average AV value using the following expression (7).

[Math. 7]

$$\text{AVERAGE } AV \text{ VALUE} = \log_2\left(\frac{1}{\text{AVERAGE } AV \text{ LIGHT AMOUNT VALUE)}}\right) \quad (7)$$

That is, first, the gain setting unit 1254 calculates a time-series change in the light amount in the exposure period of each horizontal line from the diaphragm drive locus in the exposure period of each horizontal line. Then, the average light amount in the exposure period of each horizontal line is calculated on the basis of the time-series change in the light amount. Moreover, the average light amount in the exposure period of each horizontal line is converted into the average AV value, whereby the average AV value can be calculated.

The average AV value can be more accurately calculated by being converted from the light amount change caused by the diaphragm drive locus than by simply adopting the average of the AV values at the equally divided points as the average AV value in an arbitrary line. Therefore, the accuracy of suppressing the difference in brightness and darkness in the captured image can be improved. The technique of calculating the average AV value is not limited as long as the AV value in an arbitrary line can be calculated. To speed up the calculation of the average AV value, the average of the AV values at the equally divided points in an arbitrary line may be set as is as the average AV value. As described above, the method of calculating the average AV value may be determined according to the image capture scene or the needs of the user.

The method of calculating the average AV value has been described so far. However, the technology of the present disclosure is not limited to the example of using the average AV value as a representative value of the diaphragm value in an arbitrary line. For example, an average value of the AV values at division points in an arbitrary line may be calculated without converting the light amount into the AV value, or may be calculated using an a weighted average or the like according to the degree of influence that affects the gain correction.

Here, referring to FIG. 4, the AV value decreases from the start of exposure of the uppermost line to the end of exposure of the lowermost line. At this time, regarding the average AV value of each line, the average AV value is the highest in the uppermost line, sequentially decreases toward a lower horizontal line, and is the lowest in the lowermost line. At this time, regarding the gain correction amount for each line, it is only required to set a higher value to the horizontal line having a higher average AV value in the exposure period as the gain correction amount. Thereby, a higher gain correction amount can be added to the horizontal line having a smaller light amount, which is read in the horizontal line having a higher average AV value. Therefore, the difference in brightness and darkness can be suppressed.

Further, the gain setting unit may specify a reference horizontal line having the lowest average AV value from among a plurality of horizontal lines, and set a gain correction amount according to a calculation result of a difference between the average AV value of another horizontal line and the average AV value of the reference horizontal line, for the another horizontal line among the plurality of horizontal lines. Specifically, as illustrated in the following expression (8), the gain correction amount for the m-th horizontal line may be a difference between the average AV value [m] of the m-th line and the average AV value of the reference horizontal line. By this technique, the light amount of another horizontal line approaches the light amount of the reference horizontal line having the lowest average AV value. Therefore, the difference in brightness and darkness between upper and lower portions in the captured image can be suppressed.

[Math. 8]

$$\text{GAIN CORRECTION AMOUNT } (\Delta Sv\_comp[m]) \\ = \text{AVERAGE AV VALUE } [m] - \text{AVERAGE AV VALUE [REFERENCE]} \quad (8)$$

In the present embodiment shown in FIG. 4, the horizontal line having the lowest average AV value is used as the reference horizontal line. However, the reference horizontal line is not limited to the horizontal line having the lowest average AV value and may be appropriately determined according to a favorable range of the gain correction. For example, a center line among all the horizontal lines may be set as the reference horizontal line as long as the same correction range can be corrected in a positive direction and in a negative direction by the gain correction.

Furthermore, in the present embodiment, an example in which the AV value decreases with time has been described. However, the technology of the present disclosure can be similarly applied to a case where the AV value increases with time. At this time, regarding the average AV value of each line, the average AV value is the lowest in the uppermost line, sequentially increases toward a lower horizontal line, and is the highest in the lowermost line. At this time, regarding the gain correction amount for each line, it is only required to set a higher value to the horizontal line having a higher average AV value in the exposure period as the gain.

Specifically, the gain correction may be performed by obtaining a difference between the average AV value of the reference horizontal line, where the uppermost horizontal line having the lowest average AV value is set as the reference horizontal line, and the average AV value of each horizontal line, and adding the difference to the lowermost horizontal line having the highest average AV value.

Furthermore, in the technology of the present disclosure, an example of calculating the gain correction amount on the basis of the calculated drive locus and performing the gain correction has been described. However, the gain correction amount may be calculated on the basis of a drive locus of an actually driven diaphragm and the gain correction may be performed. In this case, the gain correction amount is calculated on the basis of an actually measured value of the driven diaphragm, for a signal after exposure of all the lines is completed and readout is performed in the imaging device 1000. That is, the light amount for the actually measured value of the driven diaphragm is calculated, the average AV value of each horizontal line is calculated, and the gain correction amount may be calculated according to a calculation result of the difference between the average AV value of each horizontal line and the average AV value of the reference horizontal line. In this method, the gain correction amount can be calculated on the basis of the actually measured value of the driven diaphragm. Therefore, the accuracy of suppressing the difference in brightness and darkness is improved.

(5. Operation Flow)

Figure 7:
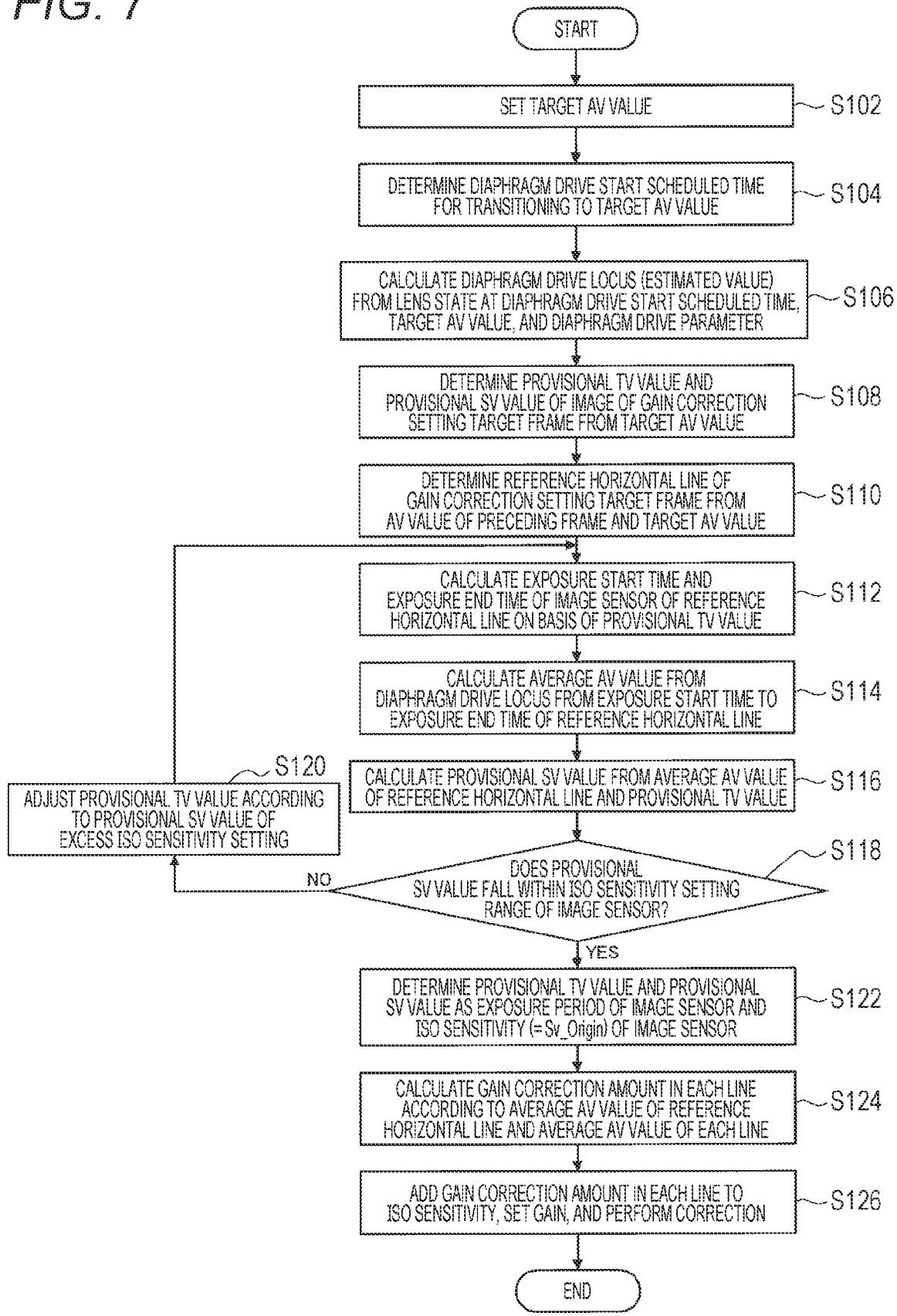
FIG. 7 is a diagram illustrating an operation flow of when gain correction is performed on the basis of a drive locus of a diaphragm.

Here, an operation flow of the above-described each configuration will be described with reference to FIG. 7. FIG. 7 is a diagram illustrating an operation flow when the gain correction is performed on the basis of the drive locus of the diaphragm.

First, the target AV value is set by the automatic exposure control function of the imaging device 1000 or by the user (S102).

Next, the diaphragm drive start scheduled time for transitioning the target AV value is determined (S104).

Further, the diaphragm drive locus is calculated from the lens state at the diaphragm drive start scheduled time, the target AV value, and the diaphragm drive parameter (S106).

Next, a provisional TV value and a provisional SV value of an image of a gain correction setting target frame are determined from the target AV value (S108). Note that the provisional TV value and the provisional SV value are provisionally determined with predetermined values.

Moreover, the reference horizontal line of the gain correction setting target frame is determined from the average AV value and the target AV value of a preceding frame of the gain correction setting target frame (S110).

Next, the exposure start time and the exposure end time on the reference horizontal line are calculated on the basis of the provisional TV value (S112).

Moreover, the average AV value of the reference horizontal line is calculated from the diaphragm drive locus from the exposure start time to the exposure end time of the reference horizontal line (S114).

Next, the provisional SV value is calculated from the average AV value and the provisional TV value of the reference horizontal line using the expression (1) (S116).

Next, whether or not the provisional SV value falls within the ISO sensitivity setting range of the image sensor is determined (S118). In a case where the provisional SV value falls within the ISO sensitivity setting range of the image sensor (S118/Yes), the process proceeds to the next processing. In a case where the provisional SV value does not fall within the ISO sensitivity setting range of the image sensor (S118/No), the provisional TV value is adjusted according to the provisional SV value of excess ISO sensitivity (S120). Then, the exposure start time and the exposure end time of the reference horizontal line are calculated again on the basis of the adjusted provisional TV value (S112), and the average AV value of the reference horizontal line is calculated again (S114). Such calculation of the average AV value of the reference horizontal line is repeated until the provisional SV value in the calculation process falls within the ISO sensitivity setting range of the image sensor.

In the case where the provisional SV value falls within the ISO sensitivity setting range of the image sensor, the provisional TV value and provisional SV value at that time are determined as the exposure period and the ISO sensitivity of the image sensor (S122).

Next, the gain correction amount is calculated according to the average AV value of the reference horizontal line and the average AV value of each line (S124). For example, the reference horizontal line having the lowest average AV value is specified from among a plurality of horizontal lines, and the gain correction amount according to a calculation result of a difference between the average AV value of another horizontal line and the average AV value of the reference horizontal line is calculated for the another horizontal line among the plurality of horizontal lines.

Next, the gain including the calculated gain correction amount is set by the gain setting unit, and the gain correction is performed (S126). Note that the calculated gain correction amount may be added to the ISO sensitivity of the reference horizontal line and set.

Figure 8:
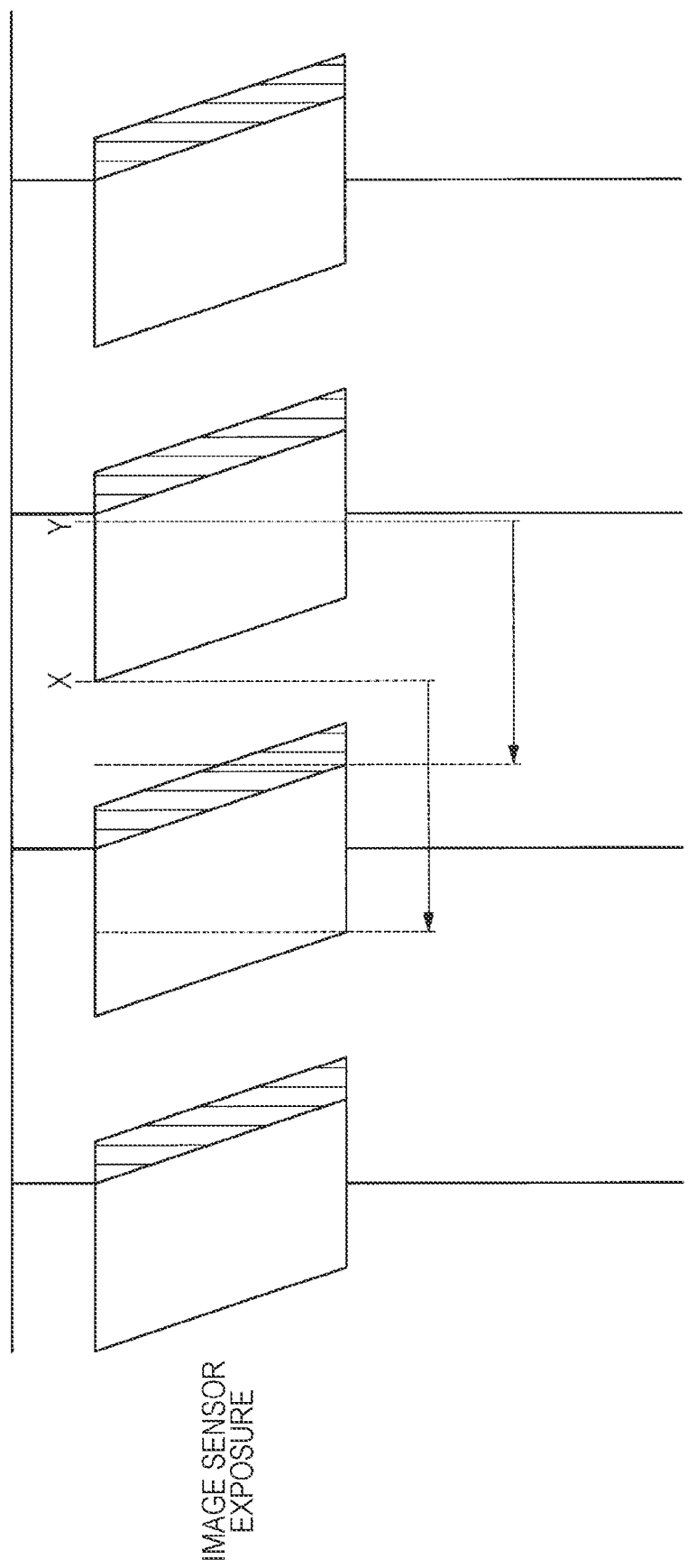
FIG. 8 is a diagram for describing an effect of the gain correction of the imaging device according to the embodiment.

An example of the operation flow in the imaging device 1000 has been described, and the gain correction has been described. Here, an effect of performing the gain correction in the imaging device to which the technology of the present disclosure is applied will be described with reference to FIG. 8. FIG. 8 is a conceptual diagram illustrating exposure and readout in the image sensor for each frame.

In the gain correction described in the example of the technology of the present disclosure, the start time of the diaphragm drive locus is determined, and the gain is set on the basis of the drive locus of the diaphragm, whereby the difference in brightness and darkness between upper and lower portions of a captured image can be accurately suppressed. For example, in the present embodiment, the gain correction amount is calculated from the setting of the provisional SV value, and the gain correction is actually reflected. To set the provisional SV value, the provisional SV value is set before a time point X at which exposure of the gain correction amount setting target frame is started, so that the imaging device can capture an image. At this time, there is a limitation due to the exposure period or a limitation due to a gain settable time.

However, in the technology of the present disclosure, the start time of the diaphragm drive locus is set. Therefore, the difference in brightness and darkness of the captured image can be accurately suppressed even if there is a limitation due to the exposure period or a limitation due to a gain settable time.

Furthermore, for the gain correction processing to be reflected in the setting target frame, there is a limitation due to the gain correction processing such that the gain is set before a time Y when the readout of the setting target frame is started, for example. However, even in this case, according to the technology of the present disclosure, the start time of the diaphragm drive locus is set, and thus the difference in brightness and darkness of the captured image can be accurately suppressed.

Moreover, conventionally, there has been no gain correction technology as in the present embodiment, so processing of delaying driving of the diaphragm, for example, has been performed so as not to cause the difference in brightness and darkness between upper and lower portions of a captured image. In the technology of the present disclosure, the gain correction can be performed on the basis of the predicted drive locus of the diaphragm. Therefore, the diaphragm can be driven faster than before. This improves the accuracy of autofocus.

In particular, in a dark place or in a case where an object has a low contrast, the light amount to be acquired is increased by lowering the diaphragm value of the imaging device, and autofocus is performed. In this case, when the technology of the present disclosure is applied, the autofocus can be performed in a state where the diaphragm is driven faster and the diaphragm value is further reduced, and the autofocus accuracy is improved.

Furthermore, the technology of the present disclosure can be applied to a state before the start of exposure of an image to be captured when a small diaphragm value is set for setting a high diaphragm value, that is, a state in which the user determines an object composition while viewing a live view. Thereby, by performing the gain correction for the captured image in the live view in a state close to the light amount of when the diaphragm value is higher, the captured image during actual image capture can be more faithfully displayed.

(6. Modification)

Figure 9:
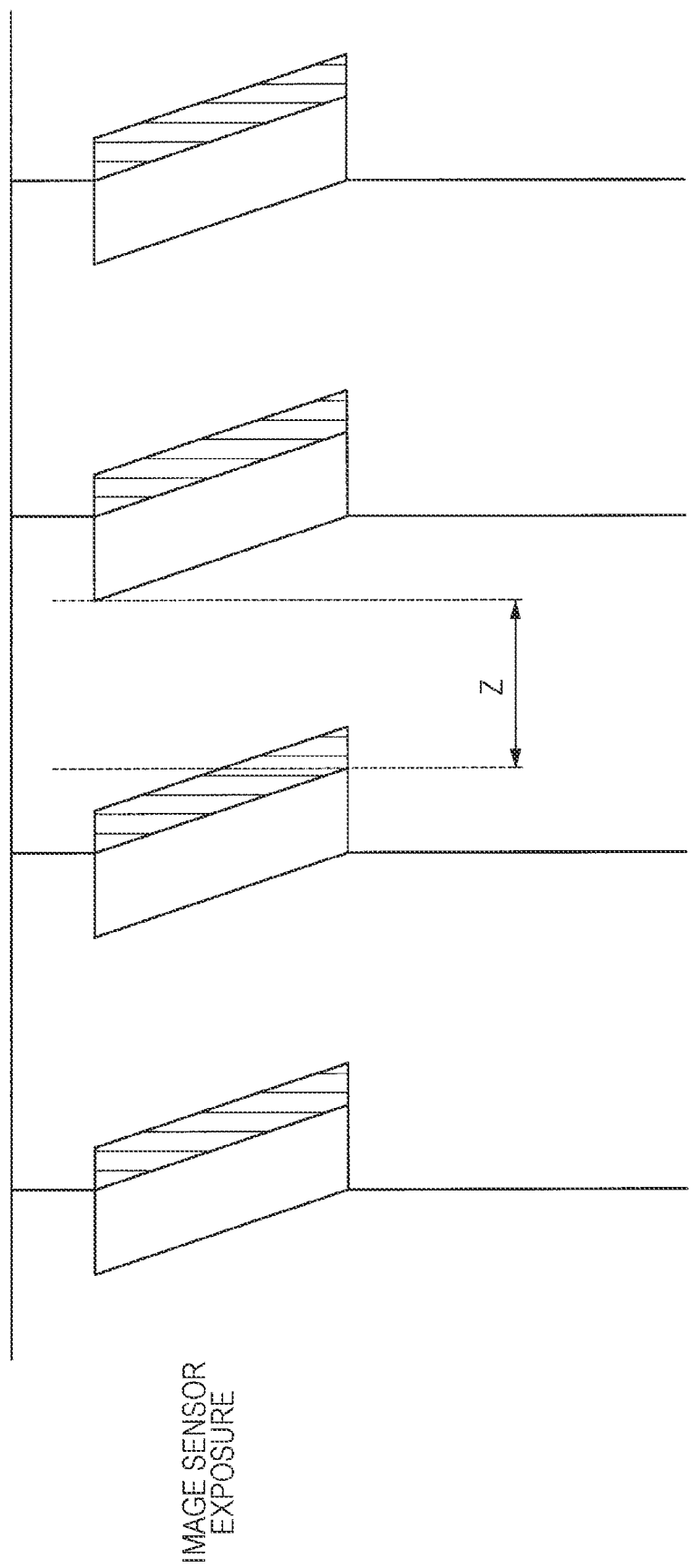
FIG. 9 is a diagram illustrating a modification of the imaging device according to the embodiment.

Next, a modification in which the imaging device 1000 performs gain correction will be described. As in a period Z illustrated in FIG. 9, the drive start time and the drive end time of the diaphragm may be set so that the driving of the diaphragm starts and ends within a period from the exposure end time of an arbitrary frame to the exposure start time of the next frame. By this technique, the driving of the diaphragm during exposure can be suppressed, and a change in an acquired light amount for each horizontal line during exposure can be suppressed.

Furthermore, in the present embodiment, the description has been made on the assumption that the lens unit and the camera unit are continuously synchronized. However, the gain correction can be performed according to the start time and end time of the diaphragm driving and the diaphragm locus information, even if there is no continuous synchronization control. For example, as an example in which there is no continuous synchronous control, first, the exposure control unit 1252 calculates the drive locus of the diaphragm and outputs the drive locus of the diaphragm to the diaphragm drive unit 1140. When the diaphragm drive unit 1140 acquires an instruction to which an instruction that the driving is started after a predetermined time from the acquisition of the drive locus of the diaphragm is added, the gain correction can be performed even if there is no continuous synchronization control. By adding the information that the driving is started after a predetermined time, the diaphragm can be driven in consideration of a delay time from the diaphragm drive instruction from the exposure control unit 1252 to when the diaphragm can be actually driven.

In a case where there is no delay time from the diaphragm drive instruction from the exposure control unit 1252 to when the diaphragm can be actually driven, the drive control unit 1120 can drive the diaphragm even if the instruction that the driving is started after a predetermined time from the acquisition of the drive locus of the diaphragm is not added.

Moreover, as a modification of the present embodiment, a case of driving the diaphragm using two types of commands: a synchronization command for performing communication in synchronization with a synchronization signal for synchronizing the lens unit and the camera unit, and an asynchronization command for performing communication at arbitrary timing without depending on the synchronization signal timing will be described. For the commands, one or more commands to be transmitted at the same timing are packetized into one packet and transmitted by packet communication. One packet includes a header, a command, and a footer, the header is added before the command, and the footer is added after the command. The footer includes a checksum for confirming the presence or absence of a command communication error on a receiving side during communication.

Here, the synchronization signal used for the synchronization command includes not only the synchronization signal itself transmitted via a synchronization signal terminal (not illustrated) provided in the lens unit or the camera unit but also frequency division or multiplication of the synchronization signal. That is, the lens unit and the camera unit perform communication on the basis of the synchronization signal or the signal obtained by dividing or multiplying the synchronization signal. Since the synchronization signal is communicated in synchronization with the synchronization signal, communication timing of a next second synchronization command after communication of a first synchronization command is performed is synchronization signal timing after the communication of the first synchronization command is performed. Furthermore, as the synchronization signal used for the synchronization command, some of the plurality of synchronization signals may be collected at irregular intervals and used for information transfer.

In contrast, the asynchronization command is used in a case where notification of occurrence of a communication error is instantly provided to the lens unit or the camera unit when the communication error has occurred in the communication using the synchronization command, for example. A case where the lens unit receives a command from the camera unit will be described as a specific example, that is, the lens unit detects the presence or absence of the communication error in the command transmitted from the camera unit by determining a checksum. In the case where the communication error is detected, the lens unit sends the fact that the communication error has occurred to the camera unit with an asynchronization command. As a result, the camera unit that has received the asynchronization command indicating that the communication error has occurred can immediately perform recovery processing for the communication error.

As described above, the lens unit and the camera unit may communicate at irregular timing different from the synchronization control interval, in addition to the synchronization control. In the case of performing the communication at irregular timing, the diaphragm drive information may be communicated in accordance with a communication standard of the lens, for example.

(7. Hardware Configuration Example)

Figure 10:
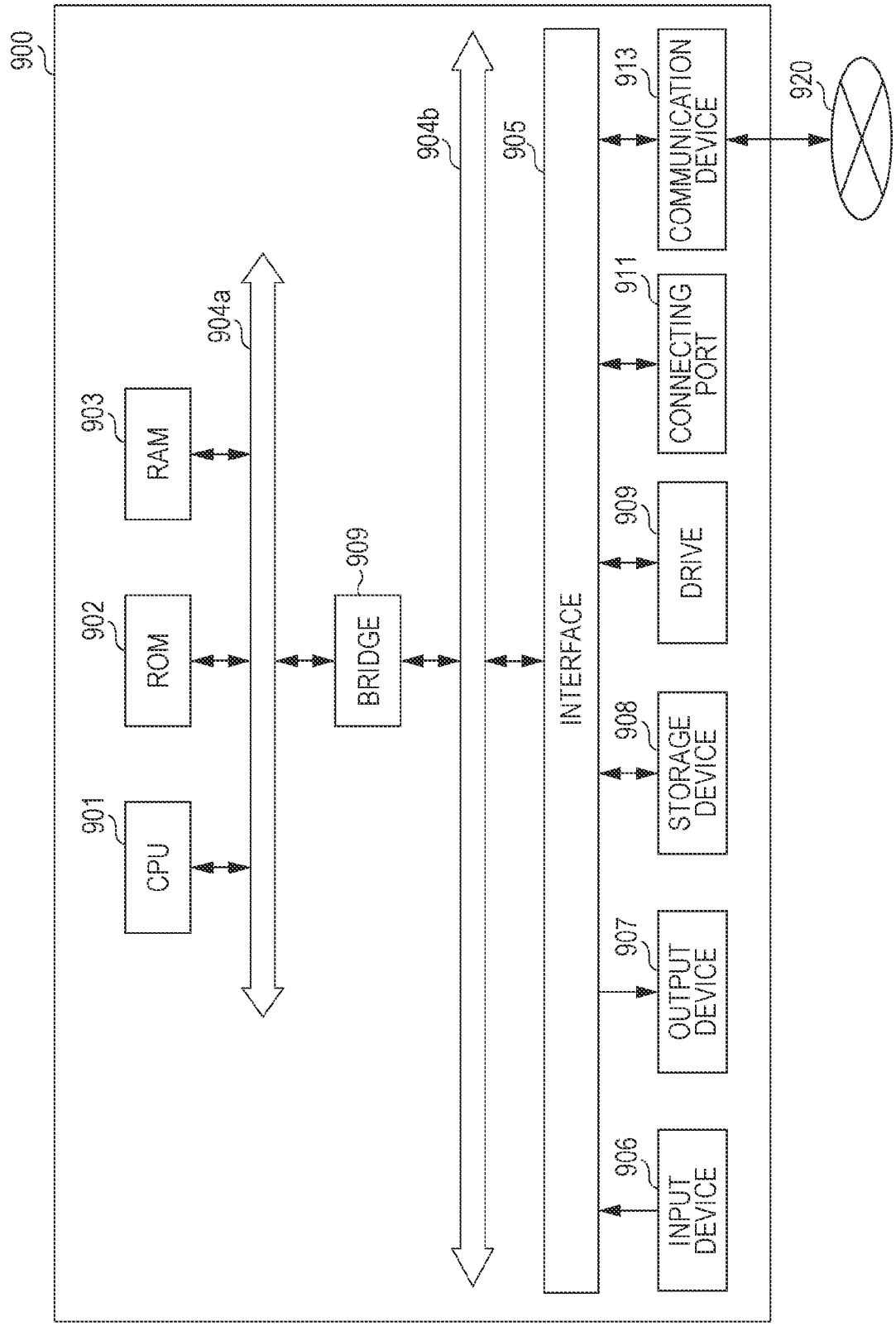
FIG. 10 is a diagram illustrating an example of a hardware configuration of the imaging device according to the embodiment.

Finally, a hardware configuration of an information processing apparatus according to the present embodiment will be described with reference to FIG. 10. FIG. 10 is a block diagram illustrating an example of a hardware configuration of an information processing apparatus according to the present embodiment. Note that an information processing apparatus 900 illustrated in FIG. 10 can implement, for example, the imaging device 1000 illustrated in FIG. 3. The information processing by the imaging device 1000 according to the present embodiment is realized by cooperation of software and hardware described below.

As illustrated in FIG. 10, the information processing apparatus 900 includes a central processing unit (CPU) 901, a read only memory (ROM) 902, a random access memory (RAM) 903, and a host bus 904a. Furthermore, the information processing apparatus 900 includes a bridge 904, an external bus 904b, an interface 905, an input device 906, an output device 907, a storage device 908, a drive 909, a connection port 911, and a communication device 913. The information processing apparatus 900 may have a processing circuit such as an electric circuit, a digital signal processor (DSP), or an application specific integrated circuit (ASIC) instead of or in addition to the CPU 901.

The CPU 901 functions as an arithmetic processing unit and a control unit, and controls an overall operation in the information processing apparatus 900 according to various programs. Furthermore, the CPU 901 may be a microprocessor. The ROM 902 stores programs, operation parameters, and the like used by the CPU 901. The RAM 903 temporarily stores programs used in the execution of the CPU 901, parameters that appropriately change in the execution, and the like. The CPU 901 can execute the functions of the diaphragm drive unit 1140 and the control unit 1250 illustrated in FIG. 3, for example.

The CPU 901, the ROM 902, and the RAM 903 are mutually connected by the host bus 904a including a CPU bus and the like. The host bus 904a is connected to the external bus 904b such as a peripheral component interconnect/interface (PCI) bus via the bridge 904. Note that the host bus 904a, the bridge 904, and the external bus 904b do not necessarily need to be separately configured, and these functions may be implemented on one bus.

The input device 906 is implemented by, for example, a device to which information is input by the user, such a touch panel, a button, a microphone, a switch, a lever, and the like. Furthermore, the input device 906 may be, for example, a remote control device using an infrared ray or another radio wave, or may be an externally connected device such as a mobile phone or a personal digital assistant (PDA) corresponding to the operation of the information processing apparatus 900. Moreover, the input device 906 may include, for example, an input control circuit that generates an input signal on the basis of the information input by the user using the above input means and outputs the input signal to the CPU 901, and the like. The user of the information processing apparatus 900 can input various data and give an instruction of processing operations to the information processing apparatus 900 by operating the input device 906.

The output device 907 is configured by a device that can visually or audibly notify the user of acquired information. Examples of such a device include display devices such as a cathode ray tube (CRT) display device, a liquid crystal display device, a plasma display device, an electroluminescence (EL) display device, a laser projector, an LED projector, and a lamp, sound output devices such as a speaker and a headphone, and the like. The output device 907 outputs, for example, results obtained by various types of processing performed by the information processing apparatus 900. Specifically, the output device 907 visually displays the results obtained by the various types of processing performed by the information processing apparatus 900 in various formats such as text, images, tables, and graphs. Meanwhile, in the case of using the sound output device, the sound output device converts an audio signal including reproduced sound data, voice data, or the like into an analog signal and aurally outputs the analog signal. The output device 907 can execute the function of the display unit 1260 illustrated in FIG. 3, for example.

The storage device 908 is a device for data storage formed as an example of a storage unit of the information processing apparatus 900. The storage device 908 is implemented by a magnetic storage device such as a hard disk drive (HDD), a semiconductor storage device, an optical storage device, a magneto-optical storage device, or the like, for example. The storage device 908 may include a storage medium, a recording device that records data in the storage medium, a reading device that reads data from the storage medium, a deletion device that deletes data recorded in the storage medium, and the like. The storage device 908 stores programs and various data executed by the CPU 901, and various data acquired from the outside, and the like. The storage device 908 is provided in, for example, the camera unit 1200 illustrated in FIG. 3 and can execute a function to store image data obtained by processing a signal acquired from the image sensor 1220, for example.

The drive 909 is a reader/writer for a storage medium, and is built in or externally attached to the information processing apparatus 900. The drive 909 reads out information recorded in a removable storage medium such as a mounted magnetic disk, optical disk, magneto-optical disk, or semiconductor memory, and outputs the information to the RAM 903. Furthermore, the drive 909 can also write information to the removable storage medium.

The connection port 911 is an interface connected to an external device, and is a connection port to an external device capable of transmitting data by a universal serial bus (USB) and the like, for example.

The communication device 913 is, for example, a communication interface including a communication device and the like for being connected to a network 920. The communication device 913 is, for example, a communication card for wired or wireless local area network (LAN), long term evolution (LTE), Bluetooth (registered trademark), wireless USB (WUSB), or the like. Furthermore, the communication device 913 may be a router for optical communication, a router for an asymmetric digital subscriber line (ADSL), a modem for various communications, or the like. The communication device 913 can transmit and receive signals and the like to and from the Internet and other communication devices in accordance with a predetermined protocol such as TCP/IP, for example. The communication device 913 can execute the functions of the communication unit 1160 and the communication unit 1270 illustrated in FIG. 3, for example.

Note that the network 920 is a wired or wireless transmission path of information transmitted from a device connected to the network 920. For example, the network 920 may include a public network such as the Internet, a telephone network, and a satellite network, various local area networks (LAN) including Ethernet (registered trademark), a wide area network (WAN), and the like. Furthermore, the network 920 may include a leased line network such as an internet protocol-virtual private network (IP-VPN).

Furthermore, a computer program for causing the hardware such as the CPU, the ROM, and the RAM built in the imaging device 1000 to exhibit functions at a similar level to the above-described configuration of the imaging device 1000 according to the present embodiment can also be created. Furthermore, a recording medium that has stored the computer program can be provided.

(8. Application)

The technology according to the present disclosure can be applied to various products. For example, the technology according to the present disclosure may be applied to the medical field or may be applied to an operating room system.

Figure 11:
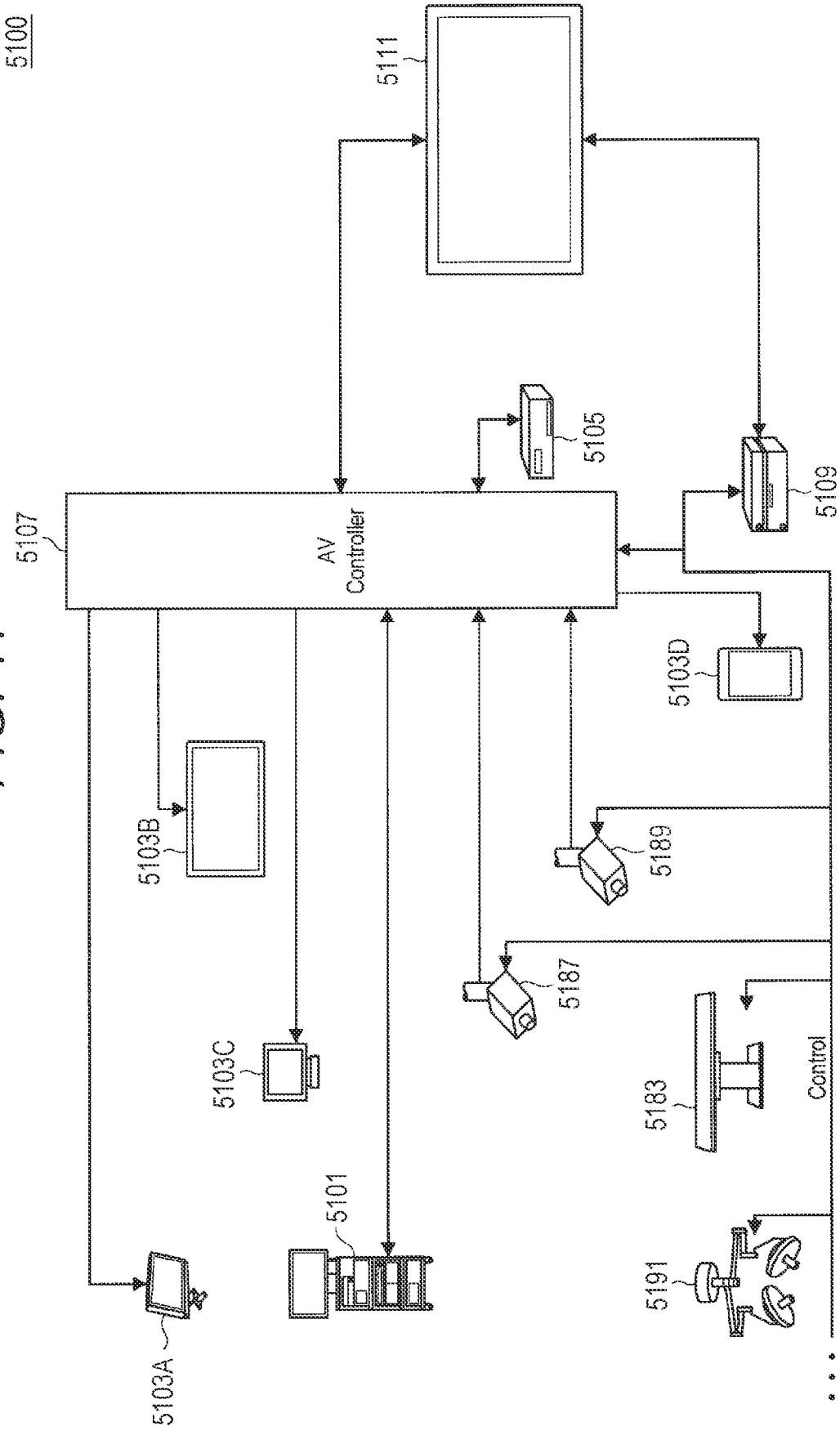
FIG. 11 is a diagram schematically illustrating an overall configuration of an operating room system.

FIG. 11 is a diagram schematically illustrating an overall configuration of an operating room system 5100 to which the technology according to the present disclosure is applicable. Referring to FIG. 11, the operating room system 5100 is configured such that devices installed in an operating room are connected to be able to cooperate with each other via an audiovisual controller (AV controller) 5107 and an operating room control device 5109.

Various devices can be installed in the operating room. FIG. 11 illustrates, as an example, a group of various devices 5101 for endoscopic surgery, a ceiling camera 5187 provided on a ceiling of the operating room and imaging the hand of an operator, a surgical field camera 5189 provided on the ceiling of the operating room and imaging an entire state of the operating room, a plurality of display devices 5103A to 5103D, a recorder 5105, a patient bed 5183, and an illumination 5191.

Here, among these devices, the group of devices 5101 belongs to an endoscopic surgical system 5113 described below and includes an endoscope, a display device that displays an image imaged by the endoscope, and the like. Each device belonging to the endoscopic surgical system 5113 is also referred to as a medical device. Meanwhile, the display devices 5103A to 5103D, the recorder 5105, the patient bed 5183, and the illumination 5191 are devices provided in, for example, the operating room separately from the endoscopic surgical system 5113. Each device not belonging to the endoscopic surgical system 5113 is referred to as a non-medical device. The audiovisual controller 5107 and/or the operating room control device 5109 controls the medical devices and the non-medical devices in cooperation with each other.

The audiovisual controller 5107 centrally controls processing relating to image display in the medical devices and the non-medical devices. Specifically, among the devices included in the operating room system 5100, the group of devices 5101, the ceiling camera 5187, and the surgical field camera 5189 can be devices (hereinafter, also referred to as devices at the transmission source) having a function to transmit information to be displayed during a surgical operation (hereinafter the information is also referred to as display information). Furthermore, the display devices 5103A to 5103D can be devices (hereinafter, also referred to as devices at the output destination) to which the display information is output. Furthermore, the recorder 5105 can be a device corresponding to both the device at the transmission source and the device at the output destination. The audiovisual controller 5107 has functions to control the operation of the devices at the transmission source and the devices at the output destination, acquire the display information from the devices at the transmission source, transmit the display information to the devices at the output destination, and display or record the display information. Note that the display information is various images imaged during the surgical operation, various types of information regarding the surgical operation (for example, physical information of a patient, information of a past examination result, information of an operation method, and the like), and the like.

Specifically, information regarding an image of an operation site in a patient's body cavity imaged by the endoscope can be transmitted from the group of devices 5101 to the audiovisual controller 5107 as the display information. Furthermore, information regarding an image of the operator's hand imaged by the ceiling camera 5187 can be transmitted from the ceiling camera 5187 as the display information. Furthermore, information regarding an image showing the state of the entire operating room imaged by the surgical field camera 5189 can be transmitted from the surgical field camera 5189 as the display information. Note that, in a case where another device having an imaging function exists in the operating room system 5100, the audiovisual controller 5107 may acquire information regarding an image imaged by the another device from the another device as the display information.

Alternatively, for example, information regarding these images imaged in the past is recorded in the recorder 5105 by the audiovisual controller 5107. The audiovisual controller 5107 can acquire the information regarding the images imaged in the past from the recorder 5105 as the display information. Note that the recorder 5105 may also record various types of information regarding the surgical operation in advance.

The audiovisual controller 5107 causes at least any of the display devices 5103A to 5103D as the devices at the output destination to display the acquired display information (in other words, the image imaged during the surgical operation and the various types of information regarding the surgical operation). In the illustrated example, the display device 5103A is a display device suspended and installed from the ceiling of the operating room, the display device 5103B is a display device installed on a wall of the operating room, the display device 5103C is a display device installed on a desk in the operating room, and the display device 5103D is a mobile device (for example, a tablet personal computer (PC)) having a display function.

Furthermore, although illustration is omitted in FIG. 11, the operating room system 5100 may include a device outside the operating room. The device outside the operating room can be, for example, a server connected to a network built inside or outside a hospital, a PC used by a medical staff, a projector installed in a conference room of the hospital, or the like. In a case where such an external device is outside the hospital, the audiovisual controller 5107 can also cause a display device of another hospital to display the display information via a video conference system or the like for telemedicine.

The operating room control device 5109 centrally controls processing other than the processing regarding the image display in the non-medical devices. For example, the operating room control device 5109 controls the driving of the patient bed 5183, the ceiling camera 5187, the surgical field camera 5189, and the illumination 5191.

The operating room system 5100 is provided with a centralized operation panel 5111, and the user can give an instruction regarding the image display to the audiovisual controller 5107 and can give an instruction regarding the operation of the non-medical devices to the operating room control device 5109, through the centralized operation panel 5111. The centralized operation panel 5111 is provided with a touch panel on a display surface of the display device.

Figure 12:
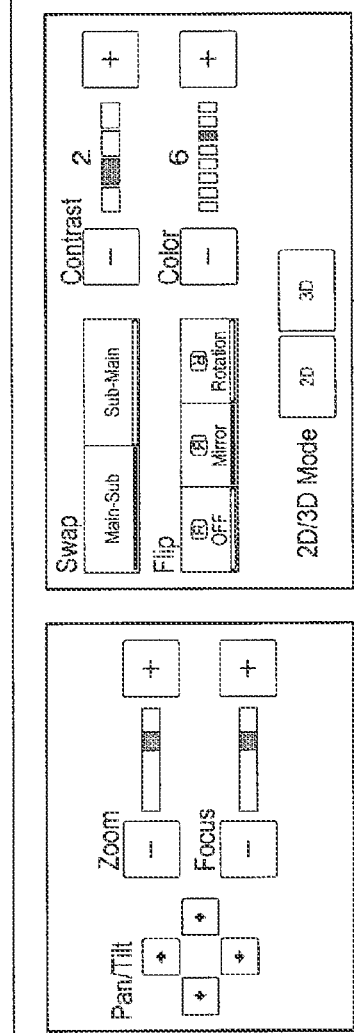
FIG. 12 is a diagram illustrating a display example of an operation screen on a centralized operation panel.

FIG. 12 is a diagram illustrating a display example of an operation screen on the centralized operation panel 5111. FIG. 12 illustrates, as an example, an operation screen corresponding to a case where two display devices are provided in the operating room system 5100 as the devices at the output destination. Referring to FIG. 12, an operation screen 5193 is provided with a transmission source selection area 5195, a preview area 5197, and a control area 5201.

The transmission source selection area 5195 displays a transmission source device provided in the operating room system 5100 and a thumbnail screen representing the display information held by the transmission source device in association with each other. The user can select the display information to be displayed on the display device from any of the transmission source devices displayed in the transmission source selection area 5195.

The preview area 5197 displays a preview of screens displayed on two display devices (Monitor 1 and Monitor 2) that are the devices at the output destination. In the illustrated example, four images are displayed in PinP on one display device. The four images correspond to the display information transmitted from the transmission source device selected in the transmission source selection area 5195. One of the four images is displayed relatively large as a main image, and the remaining three images are displayed relatively small as sub-images. The user can switch the main image and a sub-image by appropriately selecting areas where the four images are displayed. Furthermore, a status display area 5199 is provided below the areas where the four images are displayed, and the status regarding the surgical operation (for example, an elapsed time of the surgical operation, the patient's physical information, and the like) is appropriately displayed in the area.

The control area 5201 is provided with a transmission source operation area 5203 in which a graphical user interface (GUI) component for operating the device at the transmission source is displayed, and an output destination operation area 5205 in which a GUI component for operating the device at the output destination is displayed. In the illustrated example, the transmission source operation area 5203 is provided with GUI components for performing various operations (pan, tilt, and zoom) of the camera in the device at the transmission source having an imaging function. The user can operate the operation of the camera in the device at the transmission source by appropriately selecting these GUI components. Note that, although illustration is omitted, in a case where the device at the transmission source selected in the transmission source selection area 5195 is a recorder (in other words, in a case where the image recorded in the past in the recorder is displayed in the preview area 5197), the transmission source operation area 5203 can be provided with GUI components for performing operations such as reproduction, stop of reproduction, rewind, and fast forward, of the image.

Furthermore, the output destination operation area 5205 is provided with GUI components for performing various operations (swap, flip, color adjustment, contrast adjustment, and switching between 2D display and 3D display) for the display in the display device that is the device at the output destination. The user can operate the display in the display device by appropriately selecting these GUI components.

Note that the operation screen displayed on the centralized operation panel 5111 is not limited to the illustrated example, and the user may be able to perform operation input to devices that can be controlled by the audiovisual controller 5107 and the operating room control device 5109 provided in the operating room system 5100, via the centralized operation panel 5111.

Figure 13:
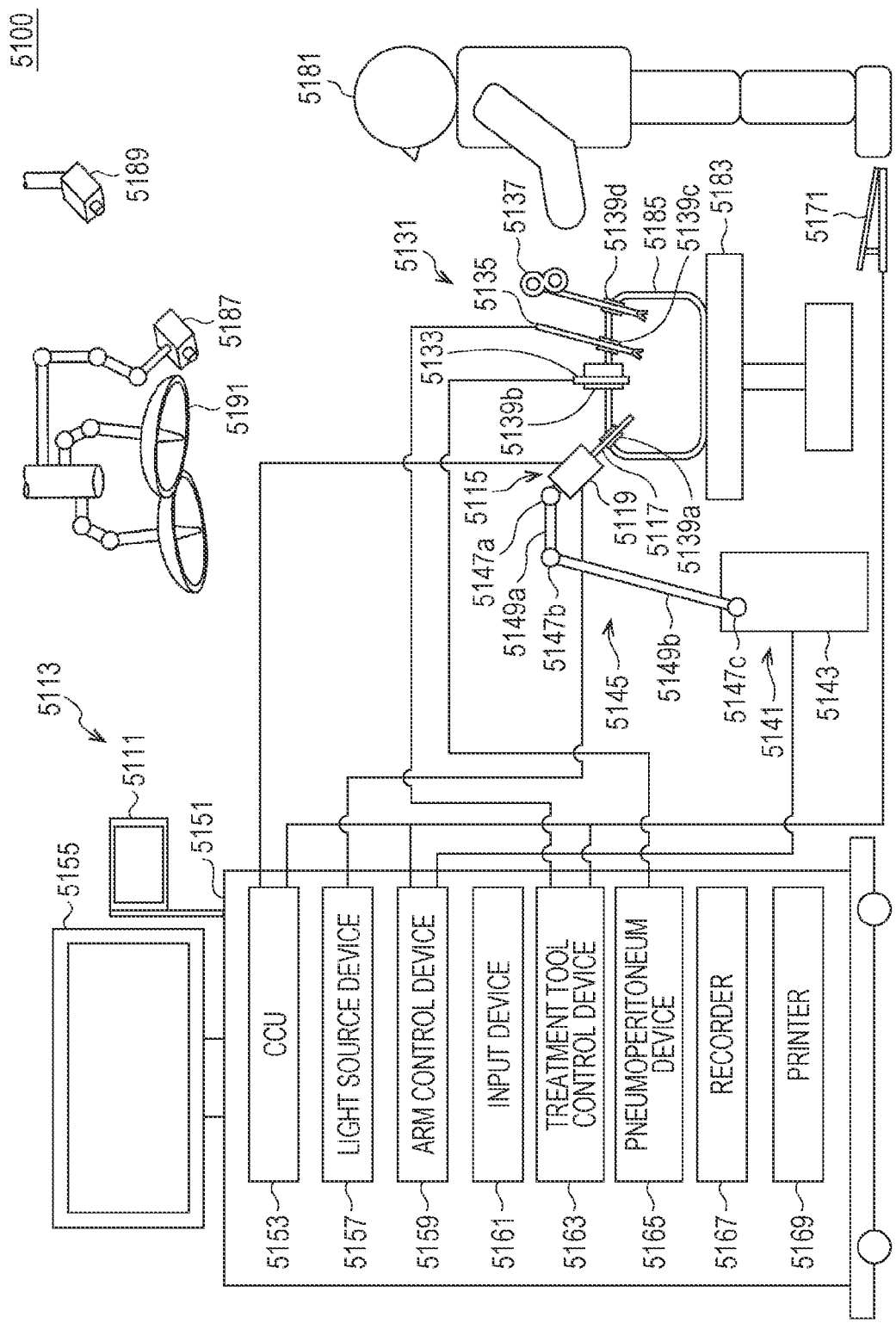
FIG. 13 is a diagram illustrating an example of a state of a surgical operation to which the operating room system is applied.

FIG. 13 is a diagram illustrating an example of a state of a surgical operation to which the above-described operating room system is applied. The ceiling camera 5187 and the surgical field camera 5189 are provided on the ceiling of the operating room and can image the hand of an operator (surgeon) 5181 who performs treatment for an affected part of a patient 5185 on the patient bed 5183 and the state of the entire operating room. The ceiling camera 5187 and the surgical field camera 5189 can be provided with a magnification adjustment function, a focal length adjustment function, an imaging direction adjustment function, and the like. The illumination 5191 is provided on the ceiling of the operating room and illuminates at least the hand of the operator 5181. The illumination 5191 may be able to appropriately adjust an irradiation light amount, a wavelength (color) of irradiation light, an irradiation direction of the light, and the like.

The endoscopic surgical system 5113, the patient bed 5183, the ceiling camera 5187, the surgical field camera 5189, and the illumination 5191 are connected in cooperation with each other via the audiovisual controller 5107 and the operating room control device 5109 (not illustrated in FIG. 13), as illustrated in FIG. 11. The centralized operation panel 5111 is provided in the operating room, and as described above, the user can appropriately operate these devices present in the operating room via the centralized operation panel 5111.

Hereinafter, a configuration of the endoscopic surgical system 5113 will be described in detail. As illustrated, the endoscopic surgical system 5113 includes an endoscope 5115, other surgical tools 5131, a support arm device 5141 that supports the endoscope 5115, and a cart 5151 in which various devices for endoscopic surgery are mounted.

In endoscopic surgery, a plurality of cylindrical puncture devices called trocars 5139*a* to 5139*d* is punctured into an abdominal wall instead of cutting the abdominal wall to open the abdomen. Then, a lens barrel 5117 of the endoscope 5115 and other surgical tools 5131 are inserted into a body cavity of the patient 5185 through the trocars 5139*a* to 5139*d*. In the illustrated example, as the other surgical tools 5131, a pneumoperitoneum tube 5133, an energy treatment tool 5135, and a pair of forceps 5137 are inserted into the body cavity of the patient 5185. Furthermore, the energy treatment tool 5135 is a treatment tool for performing incision and detachment of tissue, sealing of a blood vessel, and the like with a high-frequency current or an ultrasonic vibration. Note that the illustrated surgical tools 5131 are mere examples, and various kinds of surgical tools typically used in the endoscopic surgery such as tweezers, a retractor, and the like may be used as the surgical tools 5131.

An image of an operation site in the body cavity of the patient 5185 imaged by the endoscope 5115 is displayed on a display device 5155. The operator 5181 performs treatment such as removal of an affected part, using the energy treatment tool 5135 and the forceps 5137 while viewing the image of the operation site displayed on the display device 5155 in real time. Note that, although illustration is omitted, the pneumoperitoneum tube 5133, the energy treatment tool 5135, and the forceps 5137 are supported by the operator 5181, an assistant, or the like during the surgical operation.

(Support Arm Device)

The support arm device 5141 includes an arm unit 5145 extending from a base unit 5143. In the illustrated example, the arm unit 5145 includes joint portions 5147*a*, 5147*b*, and 5147*c*, and links 5149*a* and 5149*b*, and is driven under the control of an arm control device 5159. The endoscope 5115 is supported by the arm unit 5145, and the position and posture of the endoscope 5115 are controlled. With the control, stable fixation of the position of the endoscope 5115 can be realized.

(Endoscope)

The endoscope 5115 includes the lens barrel 5117 having a region with a predetermined length from a distal end inserted into the body cavity of the patient 5185, and a camera head 5119 connected to a proximal end of the lens barrel 5117. In the illustrated example, the endoscope 5115 configured as a so-called hard endoscope including the hard lens barrel 5117 is illustrated. However, the endoscope 5115 may be configured as a so-called soft endoscope including the soft lens barrel 5117.

The distal end of the lens barrel 5117 is provided with an opening in which an object lens is fit. A light source device 5157 is connected to the endoscope 5115, and light generated by the light source device 5157 is guided to the distal end of the lens barrel 5117 by a light guide extending inside the lens barrel 5117 and an object to be observed in the body cavity of the patient 5185 is irradiated with the light through the object lens. Note that the endoscope 5115 may be a forward-viewing endoscope, may be an oblique-viewing endoscope, or may be a side-viewing endoscope.

An optical system and an imaging element are provided inside the camera head 5119, and reflected light (observation light) from the object to be observed is condensed to the imaging element by the optical system. The observation light is photoelectrically converted by the imaging element, and an electrical signal corresponding to the observation light, that is, an image signal corresponding to an observed image is generated. The image signal is transmitted to a camera control unit (CCU) 5153 as raw data. Note that the camera head 5119 has a function to adjust magnification and a focal length by appropriately driving the optical system.

Note that, for example, to cope with stereoscopic view (3D display) or the like, a plurality of imaging elements may be provided in the camera head 5119. In this case, a plurality of relay optical systems is provided inside the lens barrel 5117 to guide the observation light to each of the plurality of imaging elements.

(Various Devices Mounted in Cart)

The CCU 5153 includes a central processing unit (CPU), a graphics processing unit (GPU), and the like, and centrally controls the operations of the endoscope 5115 and the display device 5155. Specifically, the CCU 5153 applies various types of image processing for displaying an image based on the image signal, such as developing processing (demosaic processing), to the image signal received from the camera head 5119. The CCU 5153 provides the image signal to which the image processing has been applied to the display device 5155. Furthermore, the audiovisual controller 5107 illustrated in FIG. 11 is connected to the CCU 5153. The CCU 5153 also supplies the image signal to which the image processing has been applied to the audiovisual controller 5107. Furthermore, the CCU 5153 transmits a control signal to the camera head 5119 to control its driving. The control signal may include information regarding imaging conditions such as the magnification and focal length. The information regarding imaging conditions may be input via an input device 5161 or may be input via the above-described centralized operation panel 5111.

The display device 5155 displays the image based on the image signal to which the image processing has been applied by the CCU 5153 under the control of the CCU 5153. In a case where the endoscope 5115 supports high-resolution imaging such as 4K (horizontal pixel number 3840×vertical pixel number 2160) or 8K (horizontal pixel number 7680×vertical pixel number 4320), and/or in a case where the endoscope 5115 supports 3D display, for example, the display device 5155, which can perform high-resolution display and/or 3D display, can be used corresponding to each case. In the case where the endoscope 5115 supports the high-resolution imaging such as 4K or 8K, a greater sense of immersion can be obtained by use of the display device 5155 with the size of 55 inches or more. Furthermore, a plurality of display devices 5155 having different resolutions and sizes may be provided depending on the use.

The light source device 5157 includes a light source such as a light emitting diode (LED), for example, and supplies irradiation light to the endoscope 5115 in imaging an operation site.

The arm control device 5159 includes a processor such as a CPU, and operates according to a predetermined program, thereby controlling driving of the arm unit 5145 of the support arm device 5141 according to a predetermined control method.

The input device 5161 is an input interface for the endoscopic surgical system 5113. The user can input various types of information and instructions to the endoscopic surgical system 5113 via the input device 5161. For example, the user inputs various types of information regarding the surgical operation, such as the patient's physical information and the information regarding an operation method of the surgical operation via the input device 5161. Furthermore, for example, the user inputs an instruction to drive the arm unit 5145, an instruction to change the imaging conditions (such as the type of the irradiation light, the magnification, and the focal length) of the endoscope 5115, an instruction to drive the energy treatment tool 5135, or the like via the input device 5161.

The type of the input device 5161 is not limited, and the input device 5161 may be one of various known input devices. For example, a mouse, a keyboard, a touch panel, a switch, a foot switch 5171, a lever, and/or the like can be applied to the input device 5161. In the case where a touch panel is used as the input device 5161, the touch panel may be provided on a display surface of the display device 5155.

Alternatively, the input device 5161 is, for example, a device worn by the user, such as a glass-type wearable device or a head mounted display (HMD), and various inputs are performed according to a gesture or a line-of-sight of the user detected by the device. Furthermore, the input device 5161 includes a camera capable of detecting a movement of the user, and various inputs are performed according to a gesture or a line-of-sight of the user detected from an image imaged by the camera. Moreover, the input device 5161 includes a microphone capable of collecting a voice of the user, and various inputs are performed by a sound through the microphone. The input device 5161 is configured to be able to input various types of information in a non-contact manner, as described above, so that the user (for example, the operator 5181) in particular belonging to a clean area can operate a device belonging to a filthy area in a non-contact manner. Furthermore, since the user can operate the device without releasing his/her hand from the possessed surgical tool, the user's convenience is improved.

A treatment tool control device 5163 controls driving of the energy treatment tool 5135 for cauterization and incision of tissue, sealing of a blood vessel, and the like. A pneumoperitoneum device 5165 sends a gas into the body cavity of the patient 5185 through the pneumoperitoneum tube 5133 to expand the body cavity for the purpose of securing a field of vision by the endoscope 5115 and a work space for the operator. A recorder 5167 is a device that can record various types of information regarding the surgical operation. A printer 5169 is a device that can print the various types of information regarding the surgery in various formats such as a text, an image, or a graph.

Hereinafter, a particularly characteristic configuration in the endoscopic surgical system 5113 will be further described in detail.

(Support Arm Device)

The support arm device 5141 includes the base unit 5143 as a base and the arm unit 5145 extending from the base unit 5143. In the illustrated example, the arm unit 5145 includes the plurality of joint portions 5147a, 5147b, and 5147c, and the plurality of links 5149a and 5149b connected by the joint portion 5147b. However, FIG. 13 illustrates a simplified configuration of the arm unit 5145 for simplification. In reality, the shapes, the number, and the arrangement of the joint portions 5147a to 5147c and the links 5149a and 5149b, directions of rotation axes of the joint portions 5147a to 5147c, and the like can be appropriately set so that the arm unit 5145 has a desired degree of freedom. For example, the arm unit 5145 can favorably have six degrees of freedom or more. With the configuration, the endoscope 5115 can be freely moved within a movable range of the arm unit 5145.

Therefore, the lens barrel 5117 of the endoscope 5115 can be inserted from a desired direction into the body cavity of the patient 5185.

Actuators are provided in the joint portions 5147*a* to 5147*c*, and the joint portions 5147*a* to 5147*c* are configured to be rotatable around predetermined rotation axes by driving of the actuators. The driving of the actuators is controlled by the arm control device 5159, so that rotation angles of the joint portions 5147*a* to 5147*c* are controlled and driving of the arm unit 5145 is controlled. With the control, control of the position and posture of the endoscope 5115 can be realized. At this time, the arm control device 5159 can control the driving of the arm unit 5145 by various known control methods such as force control or position control.

For example, by the operator 5181 appropriately performing an operation input via the input device 5161 (including a foot switch 5171), the driving of the arm unit 5145 may be appropriately controlled by the arm control device 5159 according to the operation input, and the position and posture of the endoscope 5115 may be controlled. With the control, the endoscope 5115 at the distal end of the arm unit 5145 can be moved from an arbitrary position to an arbitrary position, and then can be fixedly supported at the position after the movement. Note that the arm unit 5145 may be operated by a so-called master-slave system. In this case, the arm unit 5145 can be remotely operated by the user via the input device 5161 installed at a place distant from the operating room.

Furthermore, in a case where the force control is applied, the arm control device 5159 receives external force from the user, and may perform so-called power assist control to drive the actuators of the joint portions 5147*a* to 5147*c* so that the arm unit 5145 can smoothly move according to the external force. With the control, the user can move the arm unit 5145 with relatively light force when moving the arm unit 5145 while being in direct contact with the arm unit 5145. Accordingly, the user can more intuitively move the endoscope 5115 with a simpler operation, and the user's convenience can be improved.

Here, in the endoscopic surgery, the endoscope 5115 has been generally supported by a doctor called scopist. In contrast, by use of the support arm device 5141, the position of the endoscope 5115 can be reliably fixed without manual operation, and thus an image of the operation site can be stably obtained and the surgical operation can be smoothly performed.

Note that the arm control device 5159 is not necessarily provided in the cart 5151. Furthermore, the arm control device 5159 is not necessarily one device. For example, the arm control device 5159 may be provided in each of the joint portions 5147*a* to 5147*c* of the arm unit 5145 of the support arm device 5141, and the drive control of the arm unit 5145 may be realized by mutual cooperation of the plurality of arm control devices 5159.

(Light Source Device)

The light source device 5157 supplies irradiation light, which is used in imaging the operation site, to the endoscope 5115. The light source device 5157 includes, for example, an LED, a laser light source, or a white light source configured by a combination of the laser light sources. In a case where the white light source is configured by a combination of RGB laser light sources, output intensity and output timing of the respective colors (wavelengths) can be controlled with high accuracy. Therefore, white balance of a captured image can be adjusted in the light source device 5157. Furthermore, in this case, the object to be observed is irradiated with the laser light from each of the RGB laser light sources in a time division manner, and the driving of the imaging element of the camera head 5119 is controlled in synchronization with the irradiation timing, so that images each corresponding to RGB can be imaged in a time division manner. According to the method, a color image can be obtained without providing a color filter to the imaging element.

Further, driving of the light source device 5157 may be controlled to change intensity of light to be output every predetermined time. The driving of the imaging element of the camera head 5119 is controlled in synchronization with change timing of the intensity of light, and images are acquired in a time division manner and are synthesized, so that a high-dynamic range image without clipped blacks and flared highlights can be generated.

Furthermore, the light source device 5157 may be configured to be able to supply light in a predetermined wavelength band corresponding to special light observation. In the special light observation, for example, so-called narrow band imaging is performed by radiating light in a narrower band than the irradiation light (that is, white light) at the time of normal observation, using wavelength dependence of absorption of light in a body tissue, to image a predetermined tissue such as a blood vessel in a mucosal surface layer at high contrast. Alternatively, in the special light observation, fluorescence observation to obtain an image by fluorescence generated by radiation of exciting light may be performed. In the fluorescence observation, irradiating the body tissue with exciting light to observe fluorescence from the body tissue (self-fluorescence observation), injecting a reagent such as indocyanine green (ICG) into the body tissue and irradiating the body tissue with exciting light corresponding to a fluorescence wavelength of the reagent to obtain a fluorescence image, or the like can be performed. The light source device 5157 may be configured to be able to supply narrow-band light and/or exciting light corresponding to such special light observation.

(Camera Head and CCU)

Figure 14:
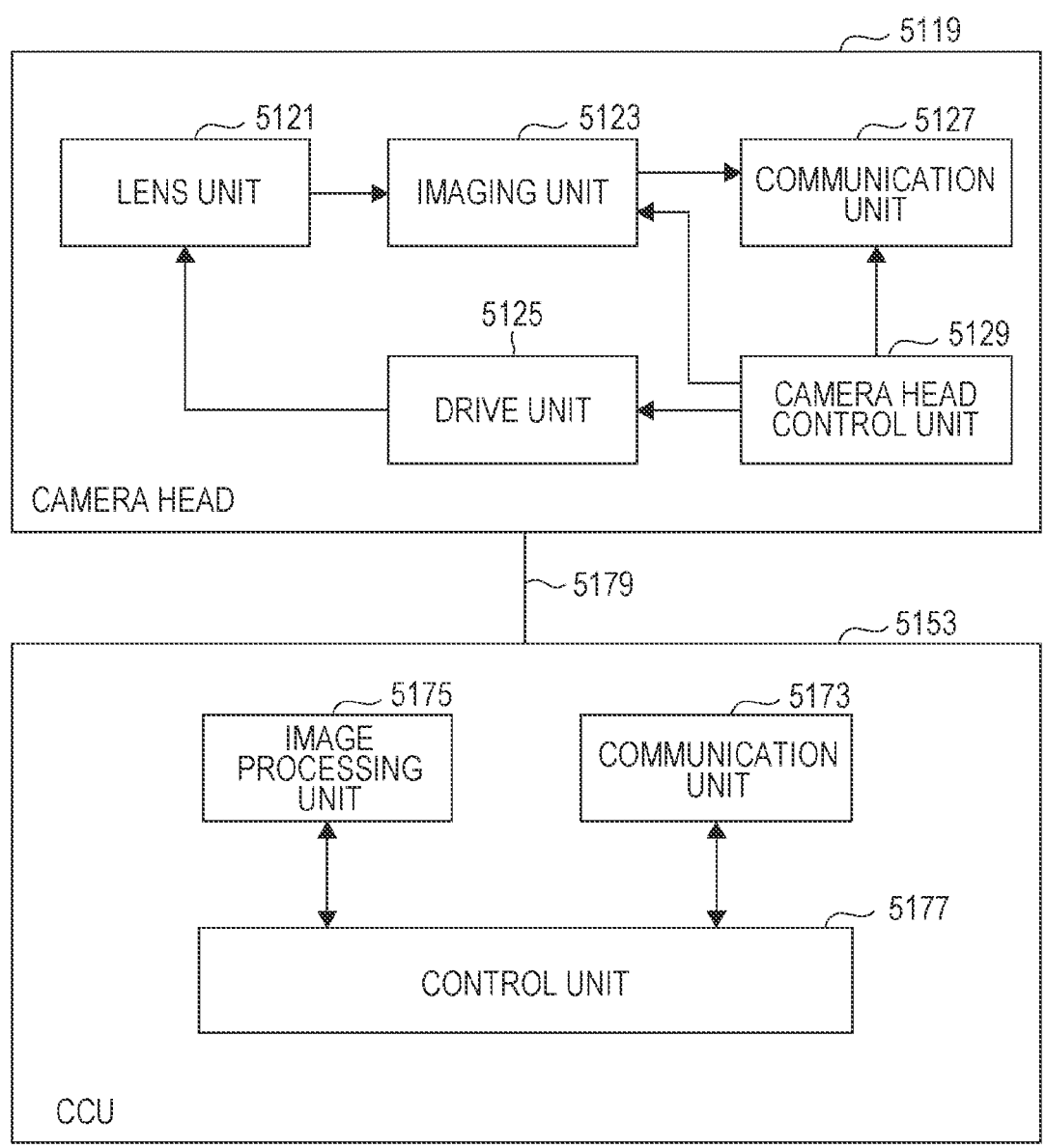
FIG. 14 is a block diagram illustrating an example of functional configurations of a camera head and a CCU illustrated in FIG. 13.

Functions of the camera head 5119 and the CCU 5153 of the endoscope 5115 will be described in more detail with reference to FIG. 14. FIG. 14 is a block diagram illustrating an example of functional configurations of the camera head 5119 and the CCU 5153 illustrated in FIG. 13.

Referring to FIG. 14, the camera head 5119 has a lens unit 5121, an imaging unit 5123, a drive unit 5125, a communication unit 5127, and a camera head control unit 5129 as its functions. Furthermore, the CCU 5153 includes a communication unit 5173, an image processing unit 5175, and a control unit 5177 as its functions. The camera head 5119 and the CCU 5153 are communicatively connected with each other by a transmission cable 5179.

First, a functional configuration of the camera head 5119 will be described. The lens unit 5121 is an optical system provided in a connection portion between the lens unit 5121 and the lens barrel 5117. Observation light taken through the distal end of the lens barrel 5117 is guided to the camera head 5119 and enters the lens unit 5121. The lens unit 5121 is configured by a combination of a plurality of lenses including a zoom lens and a focus lens. Optical characteristics of the lens unit 5121 are adjusted to condense the observation light on a light receiving surface of the imaging element of the imaging unit 5123. Furthermore, the zoom lens and the focus lens have their positions on the optical axis movable for adjustment of the magnification and focal point of the captured image.

The imaging unit 5123 includes the imaging element, and is disposed at a rear stage of the lens unit 5121. The observation light having passed through the lens unit 5121 is focused on the light receiving surface of the imaging element, and an image signal corresponding to the observed image is generated by photoelectric conversion. The image signal generated by the imaging unit 5123 is provided to the communication unit 5127.

As the imaging element configuring the imaging unit 5123, for example, a complementary metal oxide semiconductor (CMOS)-type image sensor having Bayer arrangement and capable of color imaging is used. Note that, as the imaging element, for example, an imaging element that can image a high-resolution image of 4K or more may be used. By obtainment of the image of the operation site with high resolution, the operator 5181 can grasp the state of the operation site in more detail and can more smoothly advance the surgical operation.

Furthermore, the imaging element configuring the imaging unit 5123 includes a pair of imaging elements for respectively obtaining image signals for right eye and for left eye corresponding to 3D display. With the 3D display, the operator 5181 can more accurately grasp the depth of biological tissue in the operation site. Note that, in a case where the imaging unit 5123 is configured by multiple imaging elements, a plurality of systems of the lens units 5121 may be provided corresponding to the imaging elements.

Furthermore, the imaging unit 5123 is not necessarily provided in the camera head 5119. For example, the imaging unit 5123 may be provided immediately after the object lens inside the lens barrel 5117.

The drive unit 5125 includes an actuator, and moves the zoom lens and the focus lens of the lens unit 5121 by a predetermined distance along the optical axis under the control of the camera head control unit 5129. With the movement, the magnification and focal point of the captured image by the imaging unit 5123 can be appropriately adjusted.

The communication unit 5127 includes a communication device for transmitting or receiving various types of information to or from the CCU 5153. The communication unit 5127 transmits the image signal obtained from the imaging unit 5123 to the CCU 5153 through the transmission cable 5179 as raw data. At this time, to display the captured image of the operation site with low latency, the image signal is favorably transmitted by optical communication. This is because, in the surgical operation, the operator 5181 performs the surgical operation while observing a state of an affected part with the captured image, and thus display of a moving image of the operation site in as real time as possible is demanded for a safer and more reliable surgical operation. In the case of the optical communication, the communication unit 5127 is provided with a photoelectric conversion module that converts an electrical signal into an optical signal. The image signal is converted into the optical signal by the photoelectric conversion module and is then transmitted to the CCU 5153 via the transmission cable 5179.

Furthermore, the communication unit 5127 receives a control signal for controlling driving of the camera head 5119 from the CCU 5153. The control signal includes information regarding the imaging conditions such as information for specifying a frame rate of the captured image, information for specifying an exposure value at the time of imaging, and/or information for specifying the magnification and the focal point of the captured image, for example. The communication unit 5127 provides the received control signal to the camera head control unit 5129. Note that the control signal from that CCU 5153 may also be transmitted by the optical communication. In this case, the communication unit 5127 is provided with a photoelectric conversion module that converts an optical signal into an electrical signal, and the control signal is converted into an electrical signal by the photoelectric conversion module and is then provided to the camera head control unit 5129.

Note that the imaging conditions such as the frame rate, exposure value, magnification, and focal point are automatically set by the control unit 5177 of the CCU 5153 on the basis of the acquired image signal. That is, so-called an auto exposure (AE) function, an auto focus (AF) function, and an auto white balance (AWB) function are incorporated in the endoscope 5115.

The camera head control unit 5129 controls the driving of the camera head 5119 on the basis of the control signal received from the CCU 5153 via the communication unit 5127. For example, the camera head control unit 5129 controls driving of the imaging element of the imaging unit 5123 on the basis of the information for specifying the frame rate of the captured image and/or the information for specifying exposure at the time of imaging. Furthermore, for example, the camera head control unit 5129 appropriately moves the zoom lens and the focus lens of the lens unit 5121 via the drive unit 5125 on the basis of the information for specifying the magnification and focal point of the captured image. The camera head control unit 5129 may further have a function to store information for identifying the lens barrel 5117 and the camera head 5119.

Note that the configuration of the lens unit 5121, the imaging unit 5123, and the like is arranged in a hermetically sealed structure having high airtightness and waterproofness, so that the camera head 5119 can have resistance to autoclave sterilization processing.

Next, a functional configuration of the CCU 5153 will be described. The communication unit 5173 includes a communication device for transmitting or receiving various types of information to or from the camera head 5119. The communication unit 5173 receives the image signal transmitted from the camera head 5119 through the transmission cable 5179. At this time, as described above, the image signal can be favorably transmitted by the optical communication. In this case, the communication unit 5173 is provided with a photoelectric conversion module that converts an optical signal into an electrical signal, corresponding to the optical communication. The communication unit 5173 provides the image signal converted into the electrical signal to the image processing unit 5175.

Furthermore, the communication unit 5173 transmits the control signal for controlling driving of the camera head 5119 to the camera head 5119. The control signal may also be transmitted by the optical communication.

The image processing unit 5175 applies various types of image processing to the image signal as raw data transmitted from the camera head 5119. The image processing include, for example, various types of known signal processing such as development processing, high image quality processing (such as band enhancement processing, super resolution processing, noise reduction (NR) processing, and/or camera shake correction processing), and/or enlargement processing (electronic zoom processing). Furthermore, the image processing unit 5175 performs wave detection processing for the image signal, for performing AE, AF, and AWB.

The image processing unit 5175 includes a processor such as a CPU or a GPU, and the processor operates according to a predetermined program, thereby performing the above-described image processing and wave detection processing. Note that in a case where the image processing unit 5175 includes a plurality of GPUs, the image processing unit 5175 appropriately divides the information regarding the image signal and performs the image processing in parallel by the plurality of GPUs.

The control unit 5177 performs various types of control related to imaging of the operation site by the endoscope 5115 and display of the captured image. For example, the control unit 5177 generates the control signal for controlling driving of the camera head 5119. At this time, in a case where the imaging conditions are input by the user, the control unit 5177 generates the control signal on the basis of the input by the user. Alternatively, in a case where the AE function, the AF function, and the AWB function are incorporated in the endoscope 5115, the control unit 5177 appropriately calculates optimum exposure value, focal length, and white balance according to a result of the wave detection processing by the image processing unit 5175, and generates the control signal.

Furthermore, the control unit 5177 displays the image of the operation portion or the like in the display device 5155 on the basis of the image signal to which the image processing has been applied by the image processing unit 5175. At this time, the control unit 5177 recognizes various objects in the image of the operation site, using various image recognition technologies. For example, the control unit 5177 can recognize a surgical instrument such as forceps, a specific living body portion, blood, mist at the time of use of the energy treatment tool 5135, or the like, by detecting a shape of an edge, a color, or the like of an object included in the captured image. The control unit 5177 superimposes and displays various types of surgery support information on the image of the operation site, in displaying the image of the operation site on the display device 5155, using the result of recognition. The surgery support information is superimposed, displayed, and presented to the operator 5181, so that the surgical operation can be more safely and reliably advanced.

The transmission cable 5179 that connects the camera head 5119 and the CCU 5153 is an electrical signal cable supporting communication of electrical signals, an optical fiber supporting optical communication, or a composite cable thereof.

Here, in the illustrated example, the communication has been performed in a wired manner using the transmission cable 5179. However, the communication between the camera head 5119 and the CCU 5153 may be wirelessly performed. In a case where the communication between the camera head 5119 and the CCU 5153 is wirelessly performed, it is not necessary to lay the transmission cable 5179 in the operating room. Therefore, the situation in which movement of medical staffs in the operating room is hindered by the transmission cable 5179 can be eliminated.

An example of the operating room system 5100 to which the technology according to the present disclosure is applicable has been described. Note that, here, a case in which the medical system to which the operating room system 5100 is applied is the endoscopic surgical system 5113 has been described as an example. However, the configuration of the operating room system 5100 is not limited to the example. For example, the operating room system 5100 may be applied to a flexible endoscopic system for examination or a microsurgery system, instead of the endoscopic surgical system 5113.

An application example of the medical field to which the technology according to the present disclosure is applicable has been described. The technology according to the present disclosure can be applied when the captured image processed by the CCU 5153 is displayed on the display device 5155 among the above-described configurations. For example, in the endoscopic surgical system 5113, an operation site image of the patient 5185 is displayed on the display device 5155 in real time. The operator 5181 performs treatment while viewing the image in real time. At this time, there are some cases where a light source 5157 is adjusted or the like so that the operator 5181 can easily visually recognize the operation site image. Since the light amount changes in the captured image by the adjustment of the light source 5157, processing may be applied to the captured image to suppress the difference in brightness and darkness in the captured image, using the technology according to the present disclosure.

Specifically, the gain correction of the present disclosure is executed on the live view image displayed on the above-described display device 5155 in real time. Thus, in the gain correction used for the live view image in the medical field, the gain correction amount may be calculated using the light amount of the light source.

In the live view image, the captured image can be displayed by the rolling shutter method using the CMOS image sensor, similarly to the present embodiment. For example, in a case where the light amount is insufficient for the live view image displaying the operation site of the patient 5185, the operator 5181 increases the light amount of the light source 5157 to a predetermined target light amount value. A light amount locus representing a time-series change from the current light amount value to reach the target light amount value is calculated for the target light amount value, and the gain correction amount is set for lines in the captured image on the basis of the light amount locus. The technology of the present disclosure can be similarly applied to a case of reducing the light amount. By this method, even in a case where a diaphragm is not used, the difference in brightness and darkness between upper and lower portions of the captured image can be suppressed by applying the technology of the present disclosure. In particular, the operator 5181 can comfortably perform the operation by suppressing the difference in brightness and darkness between upper and lower portions of the captured image in the above-described medical field.

Although the favorable embodiment of the present disclosure has been described in detail with reference to the accompanying drawings, the technical scope of the present disclosure is not limited to such examples. It is obvious that persons having ordinary knowledge in the technical field of the present disclosure can conceive various modifications or alterations within the scope of the technical idea described in the claims, and the modifications and alterations are naturally understood to belong to the technical scope of the present disclosure.

Furthermore, the effects described in the present specification are merely illustrative or exemplary and are not restrictive. That is, the technology according to the present disclosure can exhibit other effects obvious to those skilled in the art from the description of the present specification together with or in place of the above-described effects.

Note that following configurations also belong to the technical scope of the present disclosure.

(1)

An imaging device including: a gain setting unit configured to set a gain for each line in which a plurality of pixels is arrayed, the plurality of pixels being two-dimensionally arranged in a matrix in an image sensor, on the basis of diaphragm drive information regarding a diaphragm drive locus representing a time-series change in a diaphragm value.

(2)

The imaging device according to (1), in which the plurality of pixels is arrayed in a horizontal direction and in a vertical direction.

(3)

The imaging device according to (1) or (2), in which the plurality of pixels of the image sensor is read by a rolling shutter method for sequentially reading the pixels for each of horizontal lines arrayed in the horizontal direction.

(4)

The imaging device according to (2) or (3), in which the gain setting unit sets a higher value in a second horizontal line than in a first horizontal line as the gain, the second horizontal line having a higher average AV value in an exposure period than the first horizontal line, on the basis of the diaphragm drive locus.

(5)

The imaging device according to (4), in which the gain setting unit calculates a time-series change in a light amount in the exposure period of each horizontal line from the diaphragm drive locus in the exposure period of the each horizontal line, calculates an average light amount in the exposure period of the each horizontal line on the basis of the time-series change in the light amount, and converts the average light amount in the exposure period of the each horizontal line into an average AV value to calculate the average AV value.

(6)

The imaging device according to (4) or (5), in which the gain setting unit extracts an arbitrary horizontal line from the horizontal lines and sets the extracted horizontal line as a reference horizontal line, and sets a gain according to a calculation result of a difference between an average AV value of the reference horizontal line and an average AV value of another horizontal line.

(7)

The imaging device according to (6), in which the gain setting unit sets a horizontal line arranged in a center among the plurality of horizontal lines as a reference horizontal line, and sets a gain according to the calculation result of the difference between the average AV value of another horizontal line and the average AV value of the reference horizontal line, for the another horizontal line among the plurality of horizontal lines.

(8)

The imaging device according to (6), in which the gain setting unit sets a horizontal line having the lowest average AV value among the plurality of horizontal lines as a reference horizontal line, and sets a gain according to the calculation result of the difference between the average AV value of another horizontal line and the average AV value of the reference horizontal line, for the another horizontal line among the plurality of horizontal lines.

(9)

The imaging device according to any one of (6) to (8), in which the gain setting unit calculates provisional ISO sensitivity of the reference horizontal line on the basis of a setting value of the exposure period and the average AV value of the reference horizontal line, and adjusts the setting value of the exposure period and recalculates the average AV value of the reference horizontal line on the basis of the adjusted exposure period in a case where the provisional ISO sensitivity falls outside a range supportable by the image sensor.

(10)

The imaging device according to any one of (1) to (9), in which the diaphragm drive locus is a predicted value of the diaphragm value predicted before exposure of a setting target frame for which the gain is to be set is started.

(11)

The imaging device according to any one of (1) to (9), in which the diaphragm drive locus is an actually measured value of the diaphragm value obtained by driving a diaphragm.

(12)

The imaging device according to any one of (1) to (11), in which the diaphragm drive information regarding the diaphragm drive locus includes information regarding a time when driving of a diaphragm is started or a time when the driving of the diaphragm is terminated.

(13)

The imaging device according to any one of (1) to (12), in which the diaphragm drive information regarding the diaphragm drive locus includes information regarding a current diaphragm value of a diaphragm and a target diaphragm value targeted as the diaphragm.

(14)

The imaging device according to any one of (1) to (13), further including:

a display unit; and a gain correction unit configured to perform gain correction for the each line of a plurality of lines on the basis of the setting of the gain, in which a captured image for which the gain correction has been performed is displayed by live view on the display unit.

(15)

The imaging device according to any one of (1) to (14), further including:

a diaphragm drive control unit configured to control driving of a diaphragm; and an exposure control unit configured to calculate the diaphragm drive locus, in which the diaphragm drive control unit and the exposure control unit perform continuous communication.

(16)

A gain setting method including:

by a processor, setting a gain for each line in which a plurality of pixels is arrayed, the plurality of pixels being two-dimensionally arranged in a matrix in an image sensor, on the basis of diaphragm drive information regarding a diaphragm drive locus representing a time-series change in a diaphragm value.

(17)

A program for causing a computer to function as:

a gain setting unit configured to set a gain for each line in which a plurality of pixels is arrayed, the plurality of pixels being two-dimensionally arranged in a matrix in an image sensor, on the basis of diaphragm drive information regarding a diaphragm drive locus representing a time-series change in a diaphragm value.

REFERENCE SIGNS LIST

1000 Imaging device
1100 Lens unit
1120 Drive control unit
1140 Drive unit
1160 Communication unit 1200 Camera unit
1220 Image sensor
1230 Filter
1240 Luminance wave detection circuit
1250 Control unit
1252 Exposure control unit
1254 Gain setting unit
1256 Gain correction unit
1260 Display unit
1270 Communication unit

The invention claimed is:

1. An imaging device, comprising:
circuitry configured to:
set a gain for each horizontal line of a plurality of lines in which a plurality of pixels is arrayed, wherein
the plurality of pixels is in a two-dimensional matrix in an image sensor,
the plurality of pixels is arrayed in a horizontal direction and in a vertical direction,
the gain is set based on diaphragm drive information regarding a diaphragm drive locus representing a time-series change in a diaphragm value, and
a higher value of the gain is set in a second horizontal line than in a first horizontal line based on the diaphragm drive locus;
calculate a time-series change in a light amount in an exposure period of each horizontal line from the diaphragm drive locus in the exposure period of each horizontal line;
calculate an average light amount in the exposure period of each horizontal line based on the time-series change in the light amount; and
convert the average light amount in the exposure period of each horizontal line into an average AV value of a corresponding horizontal line, wherein the average AV value of the second horizontal line is higher than the average AV value of the first horizontal line.

2. The imaging device according to claim 1, wherein the plurality of pixels of the image sensor is read by a rolling shutter method to sequentially read a set of pixels for each horizontal line arrayed in the horizontal direction, and
the plurality of pixels includes the set of pixels.

3. The imaging device according to claim 1, wherein the circuitry is further configured to:
extract a third horizontal line from the plurality of lines;
set the extracted third horizontal line as a reference horizontal line; and
set a gain correction amount based on a calculation result of a difference between an average AV value of the reference horizontal line and an average AV value of a fourth horizontal line different from the reference horizontal line, wherein the fourth horizontal line is included in the plurality of lines.

4. The imaging device according to claim 3, wherein the circuitry is further configured to:
set a horizontal line in a center among the plurality of lines as the reference horizontal line; and
set a gain correction amount based on the calculation result of the difference between the average AV value of a fifth horizontal line different from the reference horizontal line and the average AV value of the reference horizontal line, for the fifth horizontal line among the plurality of lines.

5. The imaging device according to claim 3, wherein the circuitry is further configured to:
set a fifth horizontal line having lowest average AV value among the plurality of lines as the reference horizontal line; and
set a gain correction amount based on the calculation result of the difference between the average AV value of the fifth horizontal line and the average AV value of the reference horizontal line, for the fifth horizontal line among the plurality of lines.

6. The imaging device according to claim 3, wherein the circuitry is further configured to:
calculate provisional ISO sensitivity of the reference horizontal line based on a setting value of the exposure period and the average AV value of the reference horizontal line; and
adjust the setting value of the exposure period and recalculate the average AV value of the reference horizontal line based on the adjusted setting value of the exposure period in a case where the provisional ISO sensitivity falls outside a range supportable by the image sensor.

7. The imaging device according to claim 1, wherein the diaphragm drive locus is a predicted value of the diaphragm value predicted before exposure of a setting target frame for which the gain is to be set is started.

8. The imaging device according to claim 1, wherein the diaphragm drive locus is a measured value of the diaphragm value obtained by driving a diaphragm.

9. The imaging device according to claim 1, wherein the diaphragm drive information regarding the diaphragm drive locus includes information regarding one of a time when driving of a diaphragm is started or a time when the driving of the diaphragm is terminated.

10. The imaging device according to claim 1, wherein the diaphragm drive information regarding the diaphragm drive locus includes information regarding a current diaphragm value of a diaphragm and a target diaphragm value targeted by the diaphragm.

11. The imaging device according to claim 1, further comprising
a display unit, wherein
the circuitry is further configured to perform gain correction for each line of the plurality of lines based on the setting of the gain, and
a captured image for which the gain correction is performed is displayed by live view on the display unit.

12. The imaging device according to claim 1, wherein the circuitry is further configured to:
control driving of a diaphragm; and
calculate the diaphragm drive locus.

13. A gain setting method, comprising:
setting a gain for each horizontal line of a plurality of lines in which a plurality of pixels is arrayed, wherein
the plurality of pixels is in a two-dimensional matrix in an image sensor,
the plurality of pixels is arrayed in a horizontal direction and in a vertical direction,
the gain is set based on diaphragm drive information regarding a diaphragm drive locus representing a time-series change in a diaphragm value, and
a higher value of the gain is set in a second horizontal line than in a first horizontal line based on the diaphragm drive locus;
calculate a time-series change in a light amount in an exposure period of each horizontal line from the diaphragm drive locus in the exposure period of each horizontal line;

calculate an average light amount in the exposure period of each horizontal line based on the time-series change in the light amount; and convert the average light amount in the exposure period of each horizontal line into an average AV value of a corresponding horizontal line, wherein the average AV value of the second horizontal line is higher than the average AV value of the first horizontal line.

14. An imaging device, comprising:

circuitry configured to:

set a gain for each horizontal line of a plurality of lines in which a plurality of pixels is arrayed, wherein
the plurality of pixels is in a two-dimensional matrix in an image sensor,
the plurality of pixels is arrayed in a horizontal direction and in a vertical direction,
the gain is set based on diaphragm drive information regarding a diaphragm drive locus representing a time-series change in a diaphragm value,
a higher value of the gain is set in a second horizontal line than in a first horizontal line based on the diaphragm drive locus, and
an average AV value of the second horizontal line in an exposure period is higher than an average AV value of the first horizontal line;

extract a third horizontal line from the plurality of lines;

set the extracted third horizontal line as a reference horizontal line;

set a gain correction amount based on a calculation result of a difference between an average AV value of the reference horizontal line and an average AV value of a fourth horizontal line different from the reference horizontal line, wherein the fourth horizontal line is included in the plurality of lines;

calculate provisional ISO sensitivity of the reference horizontal line based on a setting value of the exposure period and the average AV value of the reference horizontal line;

adjust the setting value of the exposure period; and recalculate the average AV value of the reference horizontal line based on the adjusted setting value of the exposure period in a case where the provisional ISO sensitivity falls outside a range supportable by the image sensor.

\* \* \* \* \*